(12) United States Patent
Baarman

(10) Patent No.: US 11,911,530 B2
(45) Date of Patent: Feb. 27, 2024

(54) EQUIPMENT DISINFECTION

(71) Applicant: UV Partners, Inc., Grand Haven, MI (US)

(72) Inventor: David W Baarman, Fennville, MI (US)

(73) Assignee: UV Partners, Inc., Grand Haven, MI (US)

( * ) Notice: Subject to any disclaimer, the term of this patent is extended or adjusted under 35 U.S.C. 154(b) by 0 days.

(21) Appl. No.: 17/909,576

(22) PCT Filed: Mar. 5, 2021

(86) PCT No.: PCT/US2021/021032
§ 371 (c)(1),
(2) Date: Sep. 6, 2022

(87) PCT Pub. No.: WO2021/178764
PCT Pub. Date: Sep. 10, 2021

(65) Prior Publication Data
US 2023/0128052 A1    Apr. 27, 2023

Related U.S. Application Data

(60) Provisional application No. 62/986,022, filed on Mar. 6, 2020.

(51) Int. Cl.
*A61L 2/24* (2006.01)
*A61L 2/10* (2006.01)

(52) U.S. Cl.
CPC .................. *A61L 2/24* (2013.01); *A61L 2/10* (2013.01); *A61L 2202/11* (2013.01); *A61L 2202/14* (2013.01)

(58) Field of Classification Search
None
See application file for complete search history.

(56) References Cited

U.S. PATENT DOCUMENTS

2011/0309754 A1    12/2011   Ashdown et al.
2017/0296686 A1    10/2017   Cole
(Continued)

FOREIGN PATENT DOCUMENTS

| CN | 108449423 A | * | 8/2018 | ........... H04L 67/141 |
| EP | 3043244 A1 | * | 7/2016 | ............... A61L 2/10 |

(Continued)

OTHER PUBLICATIONS

International Search Report and the Written Opinion of the International Searching Authority for International Application No. PCT/US2021/021032 dated Jul. 21, 2021.

*Primary Examiner* — Andrew Smyth
(74) *Attorney, Agent, or Firm* — Warner Norcross + Judd LLP

(57) ABSTRACT

A disinfecting system and method with monitoring and safety system. The system is available at a semiconductor level with sensors for enabling effective disinfection and human machine interface functions. UV transmissive material can assist in effective distribution of UV-C light for disinfection and visible light for feedback. A replaceable sealed UV source can disinfect multiple distinct areas and be configured with a wide variety of equipment, such as medical equipment, vacuums, and cabinetry. Disinfection interlocks promote safety and efficiency.

17 Claims, 23 Drawing Sheets

(56) References Cited

U.S. PATENT DOCUMENTS

| | | | |
|---|---|---|---|
| 2019/0022263 A1* | 1/2019 | Quilici | H05B 45/10 |
| 2019/0134242 A1 | 5/2019 | Bonutti et al. | |
| 2019/0209725 A1 | 7/2019 | Henniges et al. | |
| 2019/0224353 A1 | 7/2019 | Park et al. | |

FOREIGN PATENT DOCUMENTS

| | | | | |
|---|---|---|---|---|
| KR | 2012-0076870 | | 7/2012 | |
| WO | WO-2013071042 A1 | * | 5/2013 | ............ A47L 11/00 |
| WO | 2019/241112 | | 12/2019 | |

* cited by examiner

EQUIPMENT DISINFECTION

FIELD OF THE INVENTION

The present disclosure relates to the field of disinfection, and more particularly toward disinfecting aspects, components, or surfaces of equipment while protecting users from UV.

BACKGROUND OF THE INVENTION

Many past disinfection solutions focus on mechanical isolation of a device while overdosing ultraviolet (UV) energy to increase the speed of disinfection. Other disinfection solutions focus on cleaning an entire room while humans are not present—for example terminal cleaning a patient room at a hospital in-between patients. These solutions, in their current forms are lacking, for example in they are not engineered solutions that are autonomous and convenient for users. That is, past disinfection solutions do not have ease of interaction and are not designed for intelligent automated interaction.

Use of equipment, for example office, medical, and handheld equipment, involves a user touching, positioning, or otherwise interacting with the equipment. These interactions can result in pathogens being transferred from or to a user. Disinfecting the equipment can reduce the potential for spread, but because most known disinfection solutions require active initiation and involvement from a user, all too often equipment disinfection is forgone. Further, even when disinfection solutions are engaged, equipment can be particularly difficult to effectively disinfect because pathogens can hide in various nooks and crannies of the equipment that are difficult to reach for known disinfection solutions. Further, equipment surfaces can unintentionally shield other surfaces from being disinfected. Many past solutions attempt to address these issues by increasing the amount of UV energy delivered to the equipment surface area as much as possible. However, to the extent that UV energy cannot reach a particular area due to shading or improper optical coverage, increasing the UV energy is unlikely to result in appropriate and proper treatment. These problems can be exacerbated for mobile equipment, such as carts and medical devices that have heavy use and may not have a fixed relationship with respect to a disinfection solution.

Due to its heavy and consistent user interaction, charging equipment and mobile equipment, such as smart phones and tablets, tend to have an increased pathogen level. Some disinfection solutions for charging equipment are known, but generally have major limitations. For example, reaching the full surface area of the charger and equipment being charged can be difficult. Further, doing so while being accessible to users in a human filled environment can be an issue.

Some known problems of the past disinfection technologies relate to a lack of understanding UV energy impact to equipment. The directive of "more is better" has negative ramifications to the destruction of materials not intended for intense UV exposure. Further, known solutions lack an automated process for safely providing disinfection.

SUMMARY OF THE INVENTION

In general, one innovative aspect of the subject matter described in this specification can be embodied in a disinfection and human machine interface integrated circuit. The integrated circuit includes an LED driver module configured to drive a UV LED and a visible light LED, a sensor module configured to sense a user interaction at or proximal a surface of the integrated circuit, a communications module, and a control circuit. The control circuit is coupled to the sensor module, the LED driver module, and the communication module. The control circuit is configured to provide disinfection control signals and feedback control signals to the LED driver module. The disinfection control signals operate the LED driver module, which is coupled to a UV LED, to automatically disinfect at or proximal the surface of the integrated circuit. The disinfection control signals are based, at least in part, on output from the sensor module. The feedback control signals operate the LED driver module, which is coupled to a visible light LED, to provide visual feedback. The feedback control signals are based, at least in part, on output from the sensor module.

The foregoing and other embodiments can each optionally include one or more of the following features, alone or in combination. In particular, one embodiment includes all the following features in combination.

In some embodiments, the control circuit is a state machine and the sensor module includes a capacitive touch sensor. The LED driver module can include a UV LED driver configured to drive a UV LED and a visible light LED driver configured to drive a plurality of RGB LEDs. The communications module can be configured to communicate information related to output from the sensor module that is related to disinfection, human machine interface, or both. The information can be communicated to another device according to at least one of an I2C communication protocol, a CAN communication protocol, an RF communication protocol, a digital I/O communication protocol, a Smartthings communication protocol, a Zwave communication protocol, a communication protocol Zigbee, or any combination thereof.

The sensor module is configured as a dynamic input control of a human machine interface to a separate device. The communication module is configured to transmit the dynamic input control to the separate device and receive human machine interface feedback from the device. The control circuit adapts the feedback control signals based, at least in part, on the received human machine interface feedback from the separate device. In some embodiments, the dynamic input control is at least one of a push button, rotation, slide, or switch, or any combination of these.

A touch sensor in the sensor module can be configured to sense the user interaction at or proximal a surface of the integrated circuit. The integrated circuit includes a plurality of visible light LEDs electrically coupled to the LED driver module to provide visual feedback to a user. The visual feedback can include pathogen contamination status of the surface of the integrated circuit, status types such as dirty, clean, and in progress. The visual feedback can include error feedback and human machine interface feedback.

Visual feedback can include both pathogen contamination status and human machine interface feedback. The control circuit can be configured to provide the feedback control signals for pathogen contamination status and human machine interface feedback according to a lighting feedback control scheme or circuit. The lighting visual feedback control scheme can include simultaneously indicating a pathogen contamination status by adjusting at least one of intensity, color, and blinking of the visible light LEDs and indicating human machine interface feedback by adjusting a different one of at least intensity, color, and blinking of the visible light LEDs. In some embodiments, the lighting visual feedback control scheme includes simultaneously indicating pathogen contamination status by adjusting a characteristic of one of the visible light LEDs and indicating human machine interface feedback by adjusting a characteristic of a different one of the visible light LEDs.

The sensor module can be configured as an input control of a human machine interface and the communication module is configured to communicate the input control to the separate device. The disinfection and human machine interface integrated circuit enables at least one of an automotive control input, a keyboard input, an elevator input, and a light switch input.

In some embodiments, the LED driver module includes a separate UV LED driver and a separate visible light LED driver. The control circuit can be configured to provide control signals to the visible light LED driver for providing feedback to the user regarding the human machine interface. The control circuit can be configured to monitor the sensor module and change a state of the disinfection status associated with the surface of the disinfection integrated circuit from a first status indicative of the surface being disinfected and a second status indicative of the surface being dirty. It can provide control signals to the UV LED driver for automatic disinfection in response to a combination of the disinfection status being indicative of the surface being dirty and lack of the sensor module sensing a user interaction for a predetermined period of time.

In some embodiments, the disinfection and human machine interface integrated circuit includes a plurality of terminals and a power supply and a subset of the plurality of terminals provide input power to the power supply. The power supply supplies power to the LED driver module, the sensor module, the control circuit, and the communication module. The disinfection and human machine interface integrated circuit can include a battery power supply. The battery power supply can supply power to the LED driver module, the sensor module, the control circuit, and the communication module.

The sensor module can include sensors, such as an accelerometer, a gyroscope, a capacitive touch sensor, and a time of flight sensor. The disinfection control signals are based on output from the accelerometer, the gyroscope, the capacitive touch sensor, and the time of flight sensor, and the feedback control signals are based on output from the accelerometer, the gyroscope, the capacitive touch sensor, and the time of flight sensor.

In general, another innovative aspect of the subject matter described in this specification can be embodied in a UV-C touch and feedback user interface module. The UV-C touch and feedback user interface module has a protective covering having a UV and visible light transmissive portion that forms a touch surface of the module user interface, light emitting diodes (LEDs) including a UV LED and a visible light LED, a printed circuit board joined with the protective covering and the LEDs. The printed circuit board includes a disinfection and human machine interface integrated circuit electrically coupled to the printed circuit board. The disinfection integrated circuit includes an LED driver module configured to drive the LEDs, a sensor module configured to sense a user interaction at or proximal the touch surface, a communications module configured to communicate with an external device, and a control circuit coupled to the LED driver, the sensor module, and the communication module. The control circuit is configured to provide disinfection control signals to the LED driver module for automatic disinfection at or proximal the touch surface via the UV LED transmitting UV-C light through the UV transmissive portion of the protective covering to the touch surface, and provide feedback control signals to the LED driver module for providing visual feedback via the visible light LED transmitting visible light through the protective covering to the touch surface.

The foregoing and other embodiments can each optionally include one or more of the following features, alone or in combination. In particular, one embodiment includes all the following features in combination.

In some embodiments, the printed circuit board includes a plurality of terminals and one or more supplemental interface circuits. The plurality of terminals include an input power terminal for providing power to the disinfection and human machine interface integrated circuit, and the one or more supplemental interface circuits, such as a haptic feedback circuit that provides complementary feedback to the disinfection and human machine interface integrated circuit. The haptic feedback circuit can itself include a disinfection system.

In some embodiments, the control circuit of the disinfection and human machine interface integrated circuit is configured to provide disinfection control signals to the LED driver module for automatic disinfection of the UV-C touch and feedback user interface module. This includes the touch surface and the one or more supplemental interface circuits via the UV LED transmitting UV-C light.

In some embodiments, the sensor module includes an accelerometer, a gyroscope, a capacitive touch sensor, and a time of flight sensor. The disinfection control signals can be based on output from the accelerometer, the gyroscope, the capacitive touch sensor, the time of flight sensor, or any combination thereof. The feedback control signals can also be based on output from the accelerometer, the gyroscope, the capacitive touch sensor, the time of flight sensor, or any combination thereof.

In some embodiments, the sensor module includes one or more of an accelerometer, a gyroscope, a capacitive touch sensor, and a time of flight sensor. The disinfection control signals to the LED driver module for automatic disinfection and the feedback control signals to the LED driver module are based, at least in part, on output from the one or more of the accelerometer, the gyroscope, the capacitive touch sensor, and the time of flight sensor.

The LED driver module can include a separate UV LED driver electrically coupled to the UV LED and a separate visible light LED driver coupled to the visible light LED. The control circuit is configured to provide disinfection control signals to the UV LED driver and to provide feedback control signals to the visible light LED driver. The LED driver can be configured to selectively drive the UV LED and visible light LED.

In some embodiments, the control circuit is configured to provide control signals to the LED driver module for accent lighting. The control circuit can be a state machine or timing sequence circuit. The printed circuit board can include a plurality of terminals. A subset of the plurality of terminals can be configured to provide input power from a power source external to the UV-C touch and feedback user interface module and any supplemental circuit on the printed circuit board. In some embodiments, the printed circuit board includes a battery power supply. The battery power supply supplies power to the UV-C touch and feedback user interface module and any supplemental circuit on the printed circuit board.

In some embodiments, the UV-C touch and feedback user interface module forms a fully functioning disinfecting interface for a medical device.

In some embodiments, the sensor module is configured as a dynamic input control of a human machine interface to a separate device. The communication module is configured to transmit the dynamic input control to the separate device and receive human machine interface feedback from the device, and the control circuit adapts the feedback control signals based, at least in part, on the received human machine interface feedback from the separate device. The dynamic input control can be a push button, rotation, slide, or switch, or any combination thereof.

In some embodiments, the sensor module is configured as an input control of a human machine interface and the communication module is configured to communicate the input control to the separate device. The disinfection and human machine interface integrated circuit enables at least one of an automotive control input, a keyboard input, an elevator input, a medical device input, and a light switch input.

In some embodiments, the sensor module is configured as an input control of a human machine interface and the communication module is configured to communicate the input control to the separate device. The disinfection and human machine interface integrated circuit can enable a 3D moving interface.

In general, one innovative aspect of the subject matter described in this specification can be embodied in a multi-way equipment disinfection apparatus. The multi-way equipment disinfection apparatus has a UV source configured to emit UV-C energy for disinfection. There is an enclosure surrounding the UV source. The enclosure includes a plurality of UV transmissive portions positions about the enclosure configured to enable UV-C energy transmission from the UV source to a plurality of distinct areas outside the enclosure for disinfection.

The foregoing and other embodiments can each optionally include one or more of the following features, alone or in combination. In particular, one embodiment includes all the following features in combination.

In some embodiments, the transmissive portions include a UV transmissive surface and a plurality of UV transmissive apertures. The UV transmissive surface is configured to distribute UV-C energy along a work surface of the enclosure. The plurality of UV transmissive apertures are configured to distribute UV-C energy to a plurality of devices located outside the enclosure.

In some embodiments, the apparatus includes a control circuit and a sensor module, which includes at least one of a capacitance sensor, a motion detector, an accelerometer, or any combination there. The control circuit is configured to control operation of the UV source, including activation thereof, based, at least in part, on output from the sensor module.

In some embodiments, the apparatus is a medical cart. the UV transmissive portions include a UV transmissive work surface located in a top portion of the enclosure for directing UV-C treatment along the work surface and a UV transmissive aperture in a bottom portion of the enclosure for directing UV-C energy toward a human interface device positioned on a tray below the enclosure. The human interface device positioned on the tray below the enclosure can include a keyboard and mouse.

In some embodiments, the apparatus includes a bracket joined to a side wall of the enclosure configured for removable installation of a hand-held portion of a hand-held human interface device. The bracket includes a cavity for receiving a hand-held portion of a hand-held human interface device. An internal surface of the cavity includes a UV reflective portion. The UV transmissive portions of the enclosure include a UV transmissive aperture in the side wall of the enclosure where the bracket is joined to the side wall such that a portion of UV-C energy emitted from the UV source is directed toward the cavity, and a portion of UV-C energy emitted from the UV source indirectly disinfects a hand-held portion of a hand-held human interface device installed in the bracket by virtue of reflecting off the UV reflective portion of the internal surface of the cavity.

In some embodiments, the apparatus includes a handle for moving the apparatus and a light pipe. The handle includes a hollow portion, and one of the plurality of UV transmissive portions includes a UV transmissive portion of the handle. The light pipe is routed from within the enclosure through the hollow portion of the handle. The light pipe is configured to receive UV-C energy from the UV source and transmit the UV-C energy through the light pipe toward the UV transmissive portion to disinfect an external surface of the handle.

In some embodiments, the UV source includes a plurality of UV LEDs, a control system, and a plurality of sensors that cooperate to provide automated disinfection of the plurality of areas outside the enclosure.

In some embodiments, the apparatus is a vacuum. The UV transmissive portions include a UV transmissive hose drum for directing UV-C treatment toward a vacuum hose coiled around the UV transmissive hose drum.

In some embodiments, the UV source and enclosure form a replaceable sealed UV lamp assembly. The sealed UV lamp assembly includes a wireless power receiver, and the multi-way equipment disinfection apparatus includes a wireless power transmitter for supplying wireless power to the wireless power receiver in the sealed UV lamp assembly.

The apparatus can include a wireless control system for wirelessly controlling operation of the sealed UV lamp assembly based, at least in part, on output from one or more sensors. The wireless control system is at least one of wall powered and battery powered. The wireless control system can be configured to selectively control variable UV source output and the sealed UV lamp assembly can operate according to a wireless power interlock. The wireless power link can act as both a ballast and a safety interlock.

In general, one innovative aspect of the subject matter described in this specification can be embodied in a disinfection interlock. It includes a stationary support structure including a wireless power transmitter having an inductive primary and a drawer including a wireless power receiver having an inductive secondary coupled to a UV treatment device. A pair of drawer slides, each drawer slide including a support structure profile that attaches to the stationary support structure and a drawer profile that attaches to the drawer and slides with respect to the support structure profile. The drawer is slidably configurable via the drawer slides between a closed configuration where the wireless power transmitter and the wireless power receiver are aligned to form a wireless power link for supplying power to the UV treatment device, and an open configuration where the wireless power transmitter and the wireless power receiver are unaligned such that the wireless power link is broken automatically halting any supply of power to the UV treatment device.

In some embodiments, the disinfection interlock includes a control circuit configured to delay activation of the UV treatment device in response to the drawer configuration changing to the closed configuration forming the wireless power link.

In some embodiments, the disinfection interlock includes a UV reflective surface disposed such that UV energy output by the UV treatment device reflects off the UV reflective surface and is sealed within the drawer in the closed configuration. The drawer can include a UV-C transmissive thermoform tray, with the UV treatment device being disposed under the tray and the UV reflective surface being disposed over the tray in the closed configuration such that UV energy output by the UV treatment device in the closed configuration surrounds items disposed on the tray.

The drawer can include a UV-C window that converts UV energy to visible light, providing a visual indication of the status of the UV treatment device in the closed configuration.

In some embodiments, the open configuration includes a first open configuration resulting from slidably moving the drawer from the closed configuration in a first direction. It includes a second open configuration resulting from slidably moving the drawer from the closed configuration in a second direction, opposite the first direction, wherein the pair of drawer slides are two-way drawer slides, each drawer slide having a stop. The drawer is slidably configurable via the two-way drawer slides between the first open configuration and the closed configuration. The drawer is slidably configurable via the two-way drawer slides between the second open configuration and the closed configuration.

In general, one innovative aspect of the subject matter described in this specification can be embodied in a magnetic interlock for disinfection and lighting. It has a stationary support structure including a UV source, a visible light source, a control circuit, and a support-side magnet. It has a drawer including a drawer-side magnet, wherein the support-side magnet and drawer-side magnet are installed with opposite poles facing each other. The control circuit is configured to activate the UV source in response to a magnetic link between the support-side magnet and the drawer-side magnet and interrupt the UV source in response to the magnetic link being broken between the support-side magnet and the drawer-side magnet. Both the visible light and UV-C light can have a programmable time limit. This allows the proper UV-C dose and time as well as it limits the amount of lamp life degradation for the UV-C and LED sources by limiting the on-time. In some embodiments, when opened, the timer is triggered and the visible light times out after 30 seconds. When closed, the timer retriggers the UV-C dose timer for 6 minutes. This is an exemplary time frame for proper dosage for the types of pathogens for this environment as well as a specific lamp and dose type—in other embodiments, the time frames can be varied. The control circuit is configured to de-activate the visible source in response to the magnetic link between the support-side magnet and the drawer-side magnet and activate the visible light source in response to the magnetic link being broken between the support-side magnet and the drawer-side magnet. It has a pair of drawer slides, each drawer slide including a support structure profile that attaches to the stationary support structure and a drawer profile that attaches to the drawer and slides with respect to the support structure profile. The drawer is slidably configurable via the drawer slides between a closed configuration where the drawer-side magnet and the support-side magnet are sufficiently proximal to each other to form a magnetic link for activating the UV source and deactivating the visible light, and an open configuration where the drawer-side magnet and the support-side magnet are sufficiently distal from each other to break the magnetic link for halting activation of the UV source and activating the visible light source.

The foregoing and other embodiments can each optionally include one or more of the following features, alone or in combination. In particular, one embodiment includes all the following features in combination.

In some embodiments, the magnetic interlock for disinfection and lighting include a control circuit configured to delay activation of the UV source in response to the drawer configuration changing to the closed configuration and forming the magnetic link.

In some embodiments, the magnetic interlock for disinfection and lighting include a UV transmissive tray installed, a wireless mobile phone charger, and a supplemental UV-C source in the drawer. The wireless mobile phone charger and the supplemental UV-C source are electrically coupled to the drawer-side magnet and receive power through the magnetic link. The wireless mobile phone charger and the supplemental UV-C source are installed beneath the UV transmissive tray and configured to activate in response to the closed configuration forming the magnetic link.

In general, one innovative aspect of the subject matter described in this specification can be embodied in a magnetic interlock for disinfection and lighting comprising a stationary support structure including a UV source, a visible light source, a control circuit, and a support-side magnet. It comprises a movable barrier including a barrier-side magnet, wherein the support-side magnet and barrier-side magnet are installed with opposite poles facing each other. The control circuit is configured to activate the UV source in response to a magnetic link between the support-side magnet and the barrier-side magnet and de-activate the UV source in response to a lack of the magnetic link between the support-side magnet and the barrier-side magnet. The control circuit is configured to de-activate the visible light source in response to the magnetic link between the support-side magnet and the barrier-side magnet and activate the visible light source in response to the lack of the magnetic link between the support-side magnet and the barrier-side magnet. A mechanical bearing coupling the movable barrier and the stationary support, wherein the movable barrier is movably configurable between a closed configuration where the barrier-side magnet and the support-side magnet form a magnetic link, whereby the control circuit activates the UV source and deactivates the visible light source, and an open configuration where the barrier-side magnet and the support-side magnet lack a magnetic link, whereby the control circuit deactivates the UV source and activates the visible light source.

In some embodiments, the control circuit is configured to delay activation of the UV source in response to the barrier configuration changing to the closed configuration and forming the magnetic link.

In general, one innovative aspect of the subject matter described in this specification can be embodied in an equipment disinfection system comprising equipment having a compartment for receiving a replaceable sealed UV lamp. The compartment is configured such that, when the sealed UV lamp is installed in the compartment, the sealed UV lamp is automatically configured to direct UV-C energy toward a target disinfection area of the equipment. Also included is a sealed UV lamp configured for physical reception in the compartment, wherein the sealed UV lamp includes a wireless power receiver coupled to a UV driver that supplies power to a UV source. The UV source, in response to receiving wireless power from the UV driver, emits UV-C energy to disinfect a target disinfection area of the equipment.

The sealed UV lamp assembly can be automatically configured to direct UV-C energy toward a target disinfection area of the equipment by virtue of restricting the physical reception of the sealed UV lamp to a particular orientation and position such that a reflector on the sealed UV lamp is positioned to reflect UV energy toward the target disinfection area.

In some embodiments, the sealed UV lamp is automatically configured to direct UV-C energy toward a target disinfection area of the equipment by virtue of restricting the physical reception of the sealed UV lamp to a particular orientation and position such that a wireless power receiving coil of the sealed UV lamp is aligned with a wireless power transmitting coil joined to the equipment.

In some embodiments, the equipment is a vacuum and the compartment is configured as a UV lamp receiving slot in a UV transmissive drum for storing a vacuum hose.

In some embodiments, the equipment is a medical cart and the compartment is configured as an internal compartment under a UV transmissive surface of the medical car. The UV-C energy from the sealed UV lamp disinfects the UV transmissive surface of the medical cart.

In some embodiments, the equipment is a scanner and the compartment is configured as an internal compartment in a UV transmissive handle of the scanner. The UV-C energy from the sealed UV lamp disinfects the UV transmissive handle of the scanner including a contact surface of the handle and scanner trigger.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

DESCRIPTION OF THE CURRENT EMBODIMENTS

Figure 1:
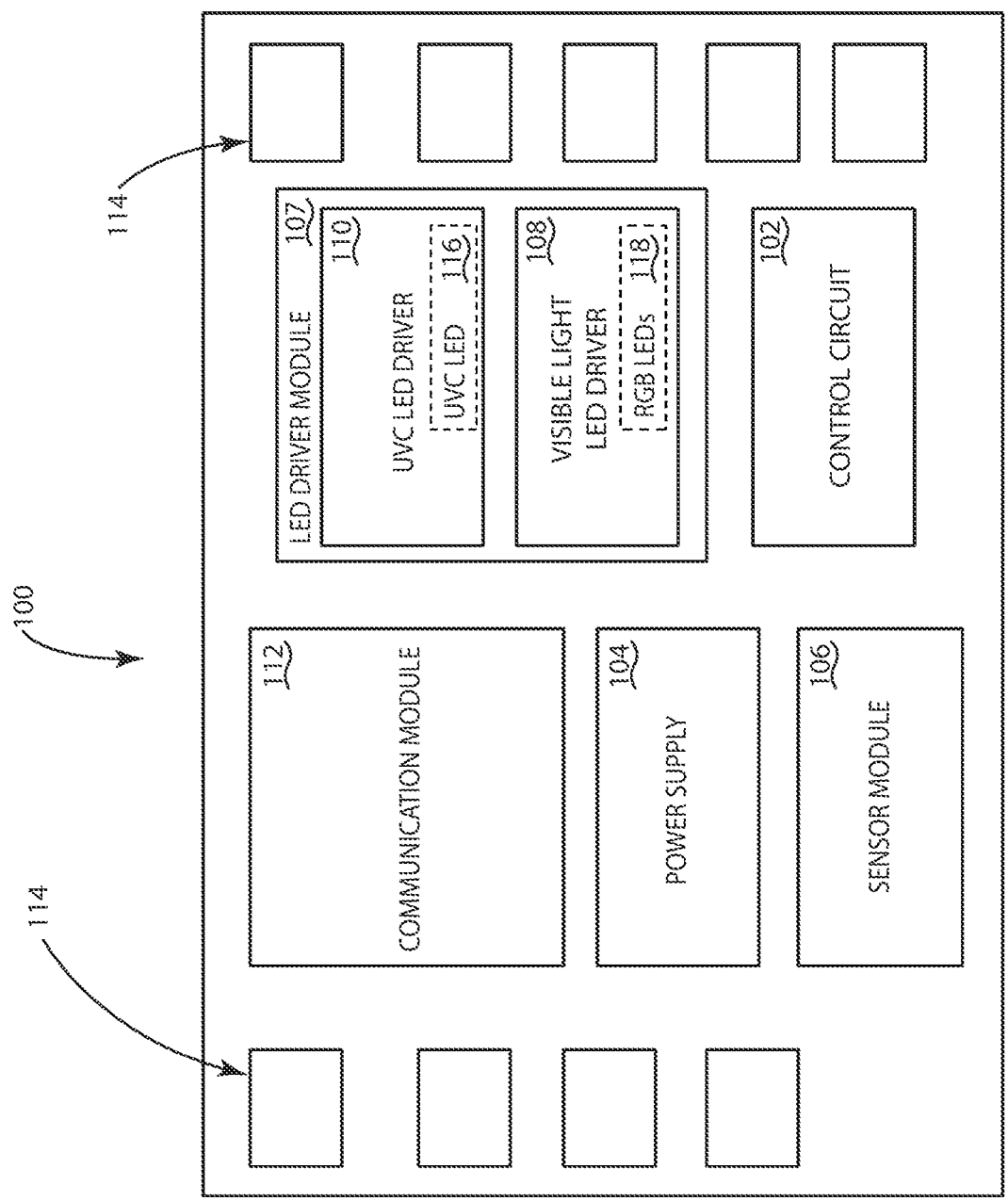
FIG. 1 illustrates a representative block diagram of a human machine interface and disinfection integrated circuit.

The various aspects and embodiments of the present disclosure involve disinfection and human machine interfaces. One aspect involves a disinfecting system and method available at a semiconductor level. The system includes user detection and sensors to detect touch and touch proximity User feedback can be provided through RGB lighting and a haptic interface. UV transmissive material assists with enabling disinfection of human machine interface while also providing an optical medium and surface for lighting and user interface. The systems and methods can involve connection to networks such as cloud based systems that enables a safer ecosystem and cross statistic sharing of safety parameters and other information.

One aspect of the present disclosure is directed to a semiconductor solution. It involves a combination of touch sensing, UV and RGB LEDs, drivers, a power supply, and a state machine with various methods of communications all packaged in a semiconductor disinfection device. This enables a push button level dynamic device that can be used as a complete human machine interface device. The touch sensor provides input, the RGB LEDs can be configured with the state machine to provide feedback, such as whether the applicable surface is clean, dirty, or in the process of being cleaned. The semiconductor feedback can also indicate errors or other types of HMI feedback as well. The communications with external devices can enable various equipment functions, including everything from automotive interfaces to keyboards, elevator buttons, and light switches.

Another aspect of the present disclosure involves incorporating the semiconductor solution into a human machine interface module. The semiconductor module can be joined with a protective cover, for example that has a button-like footprint, which enables a fully functioning disinfecting interface for use in medical or other types of equipment for use anywhere where user touches may warrant disinfection. The UV and optically transmissive layer that forms the surface of the interface can be configured to join and cooperate with the disinfection semiconductor. That is, the sensors and other functions of the semiconductor can be configured such that the module acts as slide, a switch, a rotational interface, or even as basic push buttons. Part of this can be in configuring the sensors such that they provide meaningful output indicative of manipulation of the human machine interface in a particular way. The interface module can meet the various needs of a human machine interface by sensing appropriate input and communicating it to the device being interfaced with. The module may contain several UX interface options together along with haptic and other feedback. All of the module components and surfaces can be individually disinfected or disinfected as a group. For example, a keyboard made up of a plurality of different modules may each act individually or coordinate their disinfection efforts via communication therebetween. That is, in a basic form, a module can form a simple keyboard key that provides a human machine interface for that key and disinfection for that key. In a more complex solution, multiple keyboard keys can coordinate both on providing the human machine interface and effective disinfection. In another example, UX controls, slides, and buttons in a UX may provide a 3D moving interface such as a rotating knob or levers.

Yet another aspect of the present disclosure involves controlling a UV source to provide effective disinfection to multiple different areas. By monitoring sensors, such as capacitive sensors, motion detection, and acceleration, disinfection can be effectively controlled. Using low dose UV and optics UV energy can be distributed to multiple devices and surfaces of a piece of equipment. One example, described in more detail in the disclosure, is direct to a cart that includes a UV source that can provide UV disinfecting light to an optical cart surface, to an area below the cart for disinfecting a keyboard, and to an area at the side of the cart to disinfect the handle of a scanner mounted on the cart, or other devices that receive a high number of touches. The cart handles can also be treated with the same UV source. In combination, the UV source and control system can multiple areas and surfaces providing a lower cost design with shared features and control.

Another aspect of the present disclosure relates to a wirelessly powered replaceable lamp for surface disinfection. By powering the UV lamp wirelessly, lamp replacement is simplified. Without having to connect power terminals, replacement is much easier and more practical. The lamp can also include software or hardware control that provides variable output, safety controls, and interlocks, as well as other control features. The wireless control system for may be wall powered or battery powered, which can further enable the sealing and modularization of the replaceable lamp.

Another aspect of the present disclosure is directed to modular wirelessly powered equipment, such as a medical device, with disinfection. Installation of UV disinfection systems and positioning a UV source such that UV light reaches the surface can be difficult. Using a modular approach options and modules can be added to equipment, such as medical equipment and electronic medical record carts. Subsystems can enable power transfer and monitoring can allow intelligence to be transferred from one system to the next, reducing costs. The building blocks can be combined with other systems to reduce cost while the modular approach enables the same functionality.

Another aspect of the present disclosure relates to a wireless power interlock and replacement system. A stationary portion of the interlock including the wireless transmitter and primary coil can be installed and fixed to a support structure, such as a cabinet. The moving portion can be aligned to the Tx in close proximity to a Rx mounted to the drawer, which in turn powers the systems installed in the drawer while the coils are aligned. The control system can include a short verification delay before cycling a UV dose. Separating these modular systems enhances installation and operational performance by reducing moving parts.

Another aspect of the present disclosure relates to equipment with an integral disinfection system, such as a scanner. Scanners are heavily used in medical record scanning, which enables healthcare professionals to access and manage patient information much more easily than with paper charts. By including a disinfection system in the scanner, its cradle, or the medical cart to which its holder is mounted, disinfection can be provided automatically and through routine use. For example, UV projection of an internal pattern within the scanner enclosure can be provided such that it doses over the touch surfaces. The system can dose the handle and trigger when not in use a short while after being set down. The disclosure shows disinfection as a stand externally and internally using transmissive materials, such as FEP, PFA, and Silicone MS-1000.

A gyroscope can sense tilt in accordance with attitude settings while an accelerometer can be utilized for touch sensing. The sensors can be utilized not only for control in human machine interface input and disinfection during operation, but also during setup. The gyroscope settings can be configured at installation. Then, if the parameters of the attitude change past a guard band limit, the equipment can be identified as being disturbed or damaged and a status indicator can be set as an error and appropriate action taken, such as deactivating the equipment. Further, an accelerometer on an electronic medical cart can be utilized as a primary touch detection sensor because typing segments can easily be seen. This allows the motion sensors to be used solely for safety and can tighten the ability of the system to track different activities. Understanding the movement of the cart, typing, adjusting, the can and keyboard, transferring the can from room to room, and tracking, the cleaning process, can all be valuable events to track. These events can be recognized and pushed up to the cloud for analysis and metric tracking. Having redundancy in sensor tracking can enhances the design and functionality for a safer and more accurate sensing device.

One aspect of the present disclosure relates to a semiconductor integrated circuit 100, as illustrated in FIG. 1, configured to function as both a human machine interface and disinfection device. One embodiment of the integrated circuit 100 includes a power supply 104, terminals 114, a communication module 112, an LED driver module 107 including an UV LED driver 110, a visible light LED driver 108, a sensor module 106, and a control circuit, such as state machine 102. The sensor module 106 can include a touch sensor, accelerometer, time of flight sensor, gyroscope, or any combination thereof. The semiconductor integrated circuit 100 can provide a stand-alone solution configured with the full functionality of a human machine interface as well as automated disinfection capabilities. The semiconductor 100 can be used as a standalone human machine interface, incorporated into multi-button interfaces and can be configured as rotational, slides, buttons, switches, and other human machine user interfaces.

FIG. 1 illustrates one embodiment of an integrated circuit in the form of an application specific integrated circuit (ASIC) that has the full functionality of a human machine interface and disinfection device. In the depicted embodiment, the driver module 107 includes LED drivers for programmable RGB color feedback via visible light LEDs. The LED drivers are also configured to provide UV energy for disinfection via UV LED according to a disinfection control scheme, for example whenever the sensor module senses that the interface, e.g., button, is not being pressed/interacted with. The power supply provide ideal power conditioning. The sensor module can include one or more capacitance touch sensors and an accelerometer that can provide a movement-based interface. The gyro, if included, can determine attitude and positional safety limits if moved, removed, or repositioned in predefined ways. The communication interface can include I2C communications for easily addressable user interface configurations, CAN for automotive applications and digital IO for integration with hardware directly. The communication module can also optionally include Smartthings, Zwave and Zigbee for interface with buildings and controls interfaces. Essentially any building control system communication hardware and protocol, now known or developed later, can be incorporated into the communication module 112. The semiconductor 100 can be used as stand-alone human machine interface, lighting unit, or disinfection device. Alternatively, the different features and capabilities can be combined to provide a semiconductor that can provide a human machine interface, feedback, disinfection, or any combination thereof.

The semiconductor 100 may optionally include an integrated on-chip UV LED 116 and visible light LEDs or alternatively, a UV LED and visible light LEDs can be electrically coupled to their respective drivers through terminals of the semiconductor. The UV and visible light LEDs can be driven by their respective driver circuitry according to state machine 102 logic based on, at least in part, output from the sensor module 106. For example, where the sensor module includes a capacitive or other type of touch sensor, touch sensor output can be used as input for the human machine interface with the visible light RGB LEDs providing visual feedback related to the human machine interface. The state machine 102 can be configured to track the status of the human machine interface via the sensor module 106 and trigger a disinfection cycle according to pre-defined criteria or a disinfection model stored in memory, for example in the control circuit 102. The visible light LEDs can provide visual feedback related to the status of the human machine interface, such as if a disinfection cycle is ongoing, the interface is clean, or the interface is dirty.

Capacitance touch sensors, accelerometer, time of flight sensor, and gyroscope can all provide output resulting from the user interacting with the human machine interface that can be communicated through the communication module 112, such as movement, orientation, acceleration, angular velocity, and presence information. The communication module can include a variety of different communication interfaces and communicate according to a wide variety of protocols, such as I2C, CAN, Smarthings, Zwave, and Zigbee.

The human machine interface and disinfection integrated circuit 100 can be incorporated as part of a UV-C touch and feedback user interface module 200 that has additional capabilities. In one embodiment, the module 200 includes an HMI and disinfection chip 100 as well as one or more supplemental integrated circuits configured to provide an enhanced human machine interface or to provide enhanced user feedback, such as one or more additional HMI and disinfection chips, a haptic feedback chip 206, a mechanical interface chip 204, an optics chip, or essentially any other type of integrated circuit for enhancing disinfection or the human machine interface experience. Each of which are electrically coupled together via a circuit board 202. The circuit board 202 can be joined with a UV transmissive covering 210 having a touch surface 212. The module 200 can be configured to transmit and distribute visible light and UV light through the cover to disinfect the touch surface 212 and provide feedback about one or both of the human machine interface and the surface disinfection status. The touch surface 212 can distribute both RGB light and UV light. The module 200 may add supplemental human machine interface feedback such as haptic vibration feedback and mechanical moving surfaces. In another embodiment, a hall effect sensor can be included in the HMI and disinfection sensor module (or a separate integrated circuit coupled to the printed circuit board 2020) that can be used with a physical knob having a rotating magnet such that knob position can be easily monitored to provide a meaningful human machine interface that can also be easily and automatically disinfected.

Visible light LEDs can be mounted on the HMI and disinfection chip 100, or electrically coupled through the printed circuit board terminals 208, physically positioned between the circuit board 202 and the covering 210, which can be not only UV transmissive but also visible light transmissive. The visible light LEDs can provide back lighting of the covering 210 that can be utilized in combination with printing or embedded graphic on the covering 210 in order to enhance the feedback and human machine interface provided by the chips on the circuit board 202.

The module 200 can be configured in a variety of different manners, for example as essentially any human machine interface having a touch surface that without periodic or use-based disinfection may server to facilitate spread of pathogens, such as a single button or a series of buttons. The module 200 can include functionality for programming the user interface. The module 200 can be configured in a variety of different ways to provide multiple disinfecting human machine interface configurations to accommodate almost any user interface experience while providing disinfection capabilities.

The module 200 can provide an elegant, efficient, cost-effective, and optimized size human machine interface that combines touch sensing, visible light feedback, UV disinfection, and haptic feedback along with automatic control to enable a full series of equipment disinfection capabilities. For example, one or more modules can form or being incorporated into an automotive interface, a keyboard, an elevator interface, a light switch, or essentially any other human machine interface. The module 200 can be configured to wirelessly communicate or communicate through contacts with another device to enable the human machine interface to control or interact with the other device. Although current embodiments largely utilize UV-C LEDs to produce UV-C energy for disinfection, other forms of UV energy elsewhere in the UV band can be utilized in alternative embodiments.

In another aspect of the present disclosure, one control circuit can control a single UV source to provide multiple disinfection functions. One example of this is a UV source that is configured to disinfect multiple different areas. Some embodiments are embodied by a multi-way equipment disinfection apparatus. The apparatus may include a UV source configured to emit UV-C energy for disinfection and an enclosure surrounding the UV source that includes a plurality of UV transmissive portions located about the enclosure that are configured to allow UV-C energy transmission from the UV source to a plurality of distinct areas outside the enclosure for disinfection.

Figure 3:
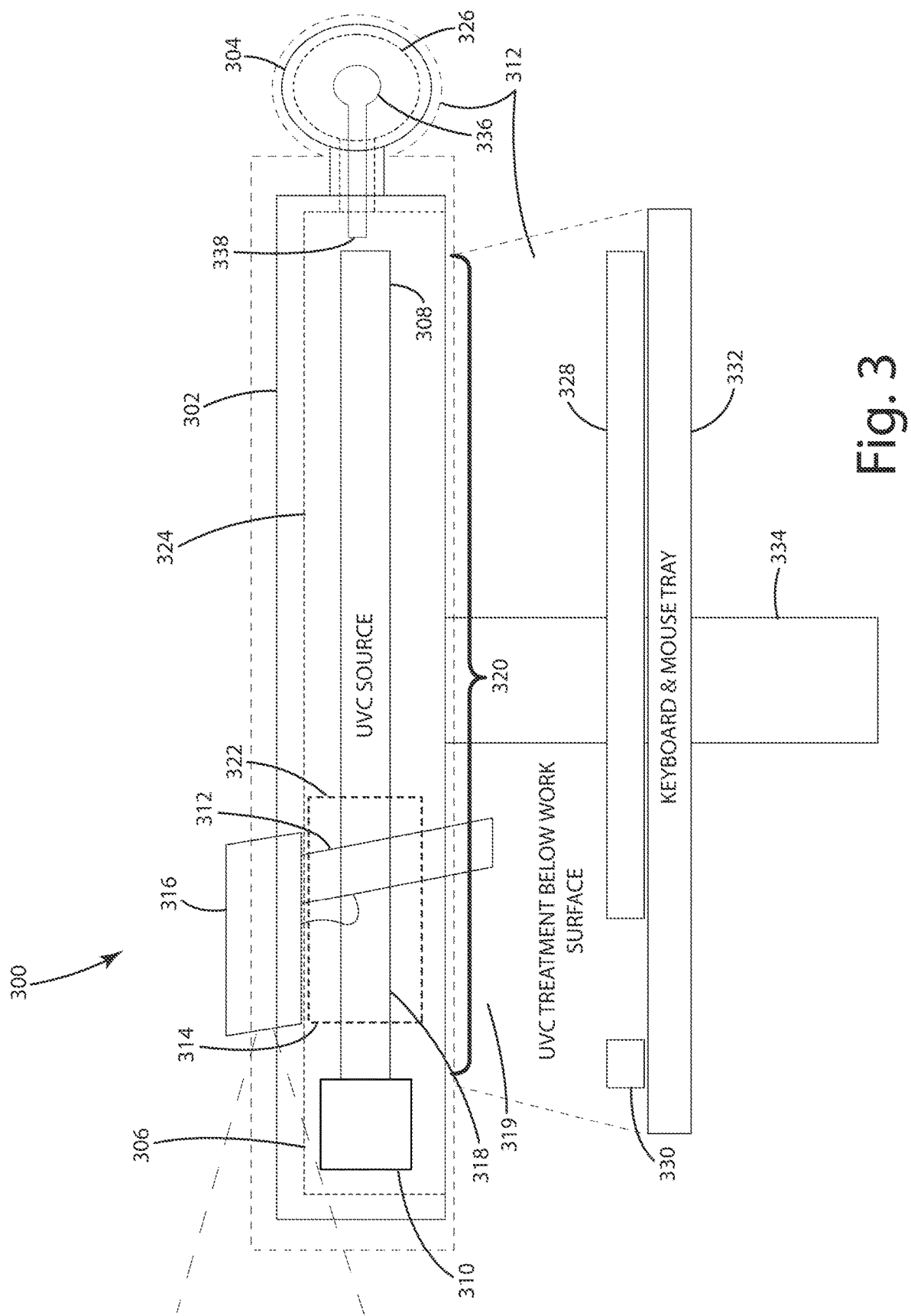
FIG. 3 illustrates a representative diagram of multi-way equipment disinfection medical cart.

One embodiment of the present disclosure is illustrated in FIG. 3. In particular, FIG. 3 illustrates a medical cart enabled with multi-way disinfection. Medical carts are typically used in healthcare facilities to store and transport medicines, medical supplies, and emergency equipment. Medical carts can be specialized for a variety of different scenarios from crash carts, isolation carts, respiratory carts to name a few. Medical carts can also be utilized for medical record entry. The carts can be made using a variety of materials, and can be modular with the ability to incorporate a variety of different medical cart accessories. Further, the medical carts can include storage bins, computers, laptops, keyboards, mice, and scanning devices. Medical carts can increase efficiency in hospitals, however, because they are mobile they also can represent an increased risk source for pathogen spread.

FIG. 3 illustrates one embodiment of a medical cart 300 that includes a work surface 302, a handle 304, a tray 332, and a post 334. The post 334 is coupled to a mobile base (not shown). A UV-C source 308 and control circuit 310 are disposed within an outer work surface 302 that forms an enclosure. The work surface 302 can include a layer of structural plastics that act as a UV transmissive layer 324 for distributing UV-C energy about the work surface 302 for disinfection. A UV transmissive layer 326 can also be positioned under or at the surface of the handles 304 for distributing UV-C energy about the handles 304 for disinfection.

Figure 4:
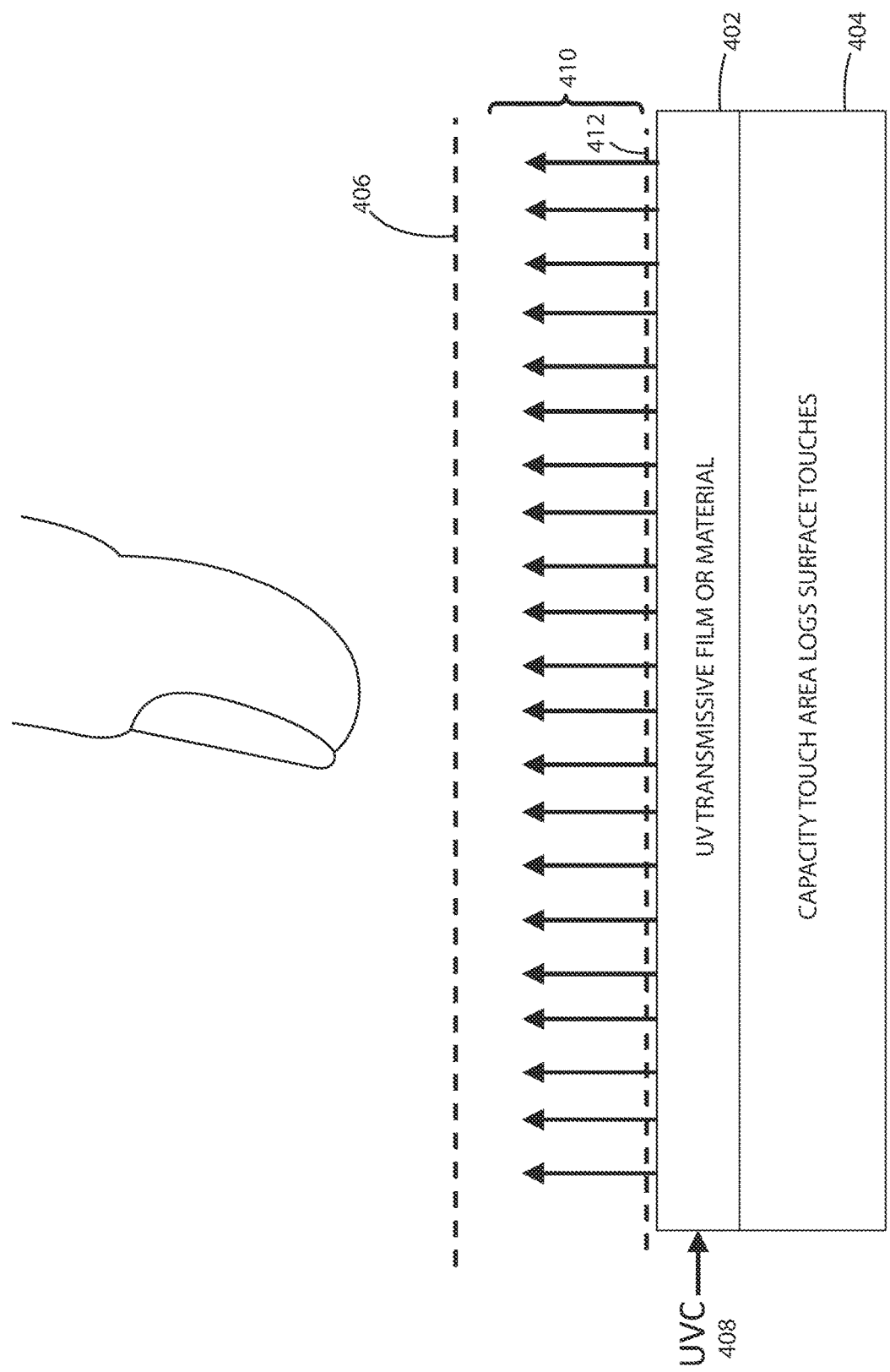
FIG. 4 illustrates a representative diagram showing capacitor touch thresholds.

The UV transmissive layer 324 can include capacitive touch conductors that run along its length, for example as depicted in FIG. 4, to enable touch detection at the work surface 302 for controlling disinfection. Put simply, FIG. 4 illustrates touch control that has a multi-level touch surface where the first detection turns off the UV and the second threshold is a touch detection. Specifically, capacitive conductors 404 can be positioned under a layer of UV transmissive film or other material 402 such that a first capacitive touch threshold 406 deactivates the UV source 408 and a second capacitive touch threshold 412 triggers the logging of a touch. The threshold distances can be configured on an application by application basis. In some embodiments, the first threshold is set such that it is triggered before a substantial amount of UV-C energy 410 reaches the distance of the threshold.

The work surface 302 can include additional UV transmissive portions of in the form of UV transmissive apertures 320, 322 as well. The regions 312 represent the UV-C energy emitted by the UV source, when activated. The UV transmissive layer 324 assists in transmission of UV-C energy along the work surface, the UV aperture 320 allows UV-C energy to shine down on the keyboard and mouse tray 332 to treat the keyboard 328 and mouse 330 sitting on the tray. While the handle 304 and the scanner 316 utilize optics and transmissive materials strategically within the product configuration to be supplied with UV-C energy from the UV source. A UV collector 338 can provide UV-C energy from the source 308 to light pipe 336, which can distribute the UV-C energy along the UV transmissive layer 326 of the handle 304. UV aperture 322 can allow UV energy to reach a UV chamber formed by the scanner bracket 314, which is mounted to the side of the medical cart 300. A portion of the UV chamber wall can include a reflective surface or coating. The chamber can include an opening at the top for inserting the handle end of the scanner 316.

Figure 5:
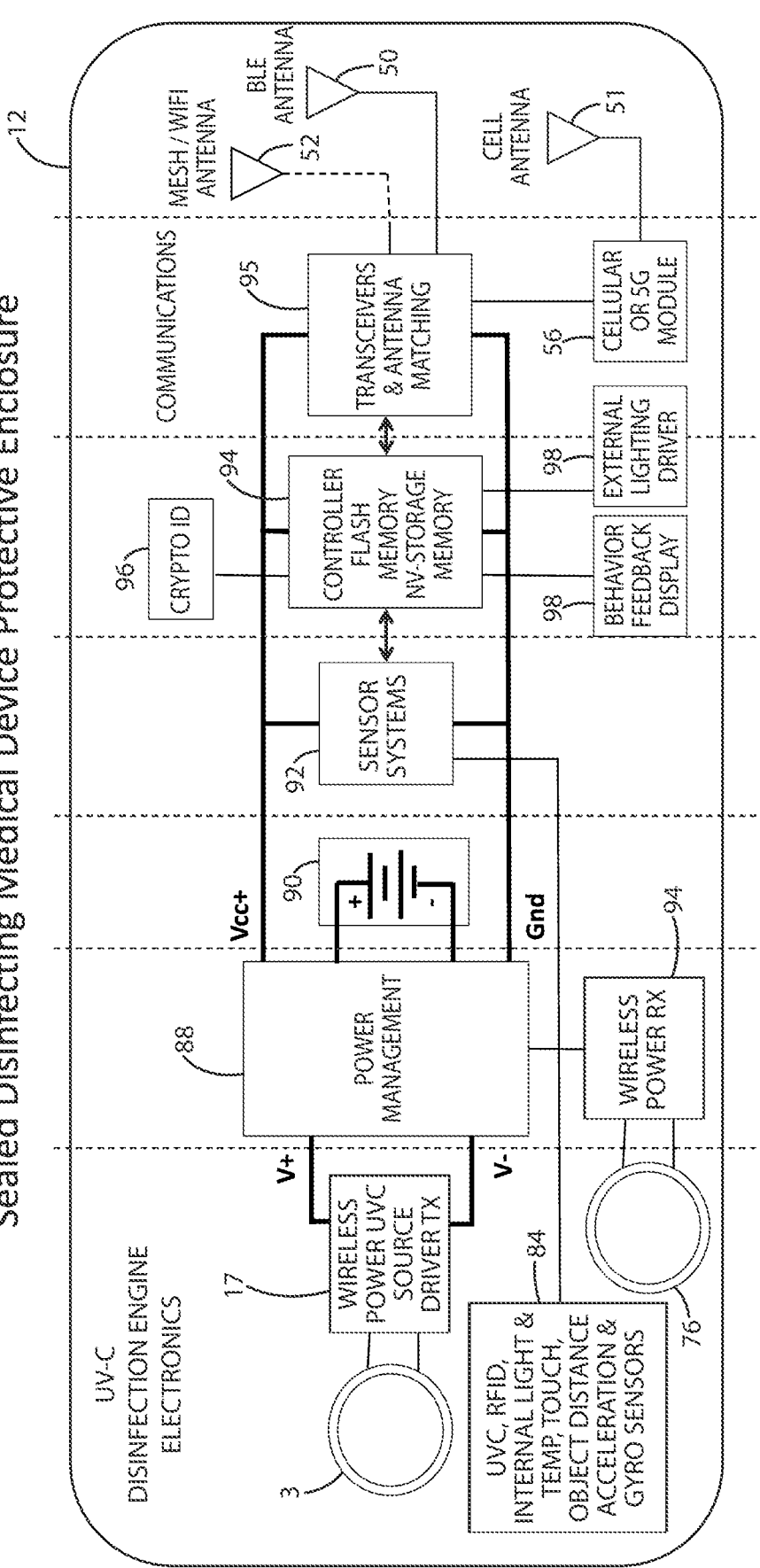
FIG. 5 illustrates a representative block diagram of one embodiment of a sealed UV lamp assembly.

FIG. 5 illustrates an embodiment of a sealed UV disinfection engine with protective enclosure 12, which can be utilized in connection with medical equipment and other equipment. The electronics can include a variety of different components and a variety of configurations. In one embodiment, the sealed UV engine includes the ability to provide wirelessly powered disinfection with battery backup. A variety of different sensors can be included within the enclosure, such as an accelerometer, gyroscope, touch sensors, distance sensors, temperature sensors, and essentially any other sensor that can provide feedback to the disinfection engine. For example, the accelerometer and gyroscope can provide feedback in connection with position and control.

The exemplary control system will now be described in detail in connection with the representative block diagram of FIG. 5. The control system can take the form of a sealed electronics package. The control system includes a disinfection device circuit that includes a controller 94 or processor that controls operation of the various components. The disinfection device circuit in the depicted embodiment includes a plurality of components installed on a printed circuit board assembly.

The disinfection device can include a battery 90 and wireless power receiver 94 to eliminate through physical input ports in the disinfection device 12. The system can include an RFID tag and a lamp driver 17 for the UVC source 3. The RFID tag can be positioned such that when the enclosure 12 is installed in equipment, the RFID tag 40 is in proximity to and can be read by an RFID reader in the equipment. Alternatively, the equipment may not include an RFID reader, and instead the tag 84 can be read by another device after removal from the equipment. The controller 94 can accept sensor input from the sensor system 92, 84 which can include a UV sensor, a light sensor, temperature sensor, distance sensor, object sensor, a touch sensor, a gyroscope, RFID, and a variety of other suitable sensors, or any combination thereof. The unit can be Internet of Things capable and can utilize BTLE, cellular and WiFi for secure crypto communications and monitoring. The system can include an RGB LED display for communicating operation status and error codes. The control system may include non-volatile memory for tracking dates used, durations and lamp hours and lamp starts, life data, and end of life counter for battery and lamp.

Referring to the communication circuitry, the disinfection device circuit can include communication circuitry 95, which can include one or more transceivers and antenna matching circuitry, such as a Mesh/Wifi antenna 52, a Bluetooth LE antenna 50, and/or a module 56 and accompanying cellular antenna 51. For example, the transceiver can be a WiFi, BTLE, BTLE Industrial, 400 or 900 Mhz transceiver. LTE or 5G+ modules make this cost effective and highly mobile. IoT solutions may not require setup and paring with these technologies in the future. BTLE can be used for monitoring devices within proximity to the disinfection device. The cellular module can be provided for advanced hub use. The antennas can all optionally be routed outside of the housing 12. Alternatively, the antennas can be chip type antennas located on the printed circuit board assembly, or otherwise positioned within the housing 12 of the disinfection device.

The disinfection circuit can include a crypto ID circuit 96, a feedback display 98, and an external lighting driver 99. The control system may also include a physical or virtual user interface. The controller can also allow external communications and interface via the transceiver 95. The controller can also operate the feedback display and external lighting driver to provide user feedback.

The sealed disinfection engine 12 can include one or more sensors as part of a sensor system 84, 92 with one or more sensors that provide sensor output to the controller 94 or elsewhere within the disinfection device circuit. The sensor system 84, 92 can include a variety of different sensors, as discussed above. Sensor data can be communicated to a database and can be shared via crypto security.

The sensor system 84, 92 can also include one or more motion sensors, such as an accelerometer. In other embodiments, the controller 94 itself can also include an accelerometer that can measure acceleration of the device. An accelerometer can be utilized to track movement of the enclosure or the equipment in which the enclosure is installed. The controller can also include capacitive and voltage sensors, in addition to such sensors included elsewhere in the disinfection device sensor systems 84, 92. A touch sensor can be used for determining disinfection control, but also for setup and configuration of the UI/UX. The voltage sensors can be used to assure proper battery voltage and wireless charging status. The sensors can assist with power management for the proper operation and maintenance of the device.

The disinfection device may include a battery or other power source 90. The battery can be sized to provide sufficient power to operate the disinfection engine for the typical duration of the use of a medical cart.

The disinfection device may also include a wireless charging system 94 that includes a wireless power receiver 76, such as an inductive coil, that can receive wireless power from a wireless power charger. By providing wireless charging of the battery, the housing 12 can be provided as a waterproof protective enclosure.

The disinfection circuit may include a power management system 88. The power management system or power supply produces a regulated power source when voltage from the battery is present.

Controller 94 can configure the UV lamp driver or UV power source 17 to provide a particular intensity that can deliver a UV dose under the ISO standard for a predetermined period of time. The controller 94 can monitor the UV dosage levels, for example, over an eight hour period or other time period, using a real time clock, for example onboard the controller. Data can be accumulated in a non-volatile accumulator and reported over time.

Figure 6:
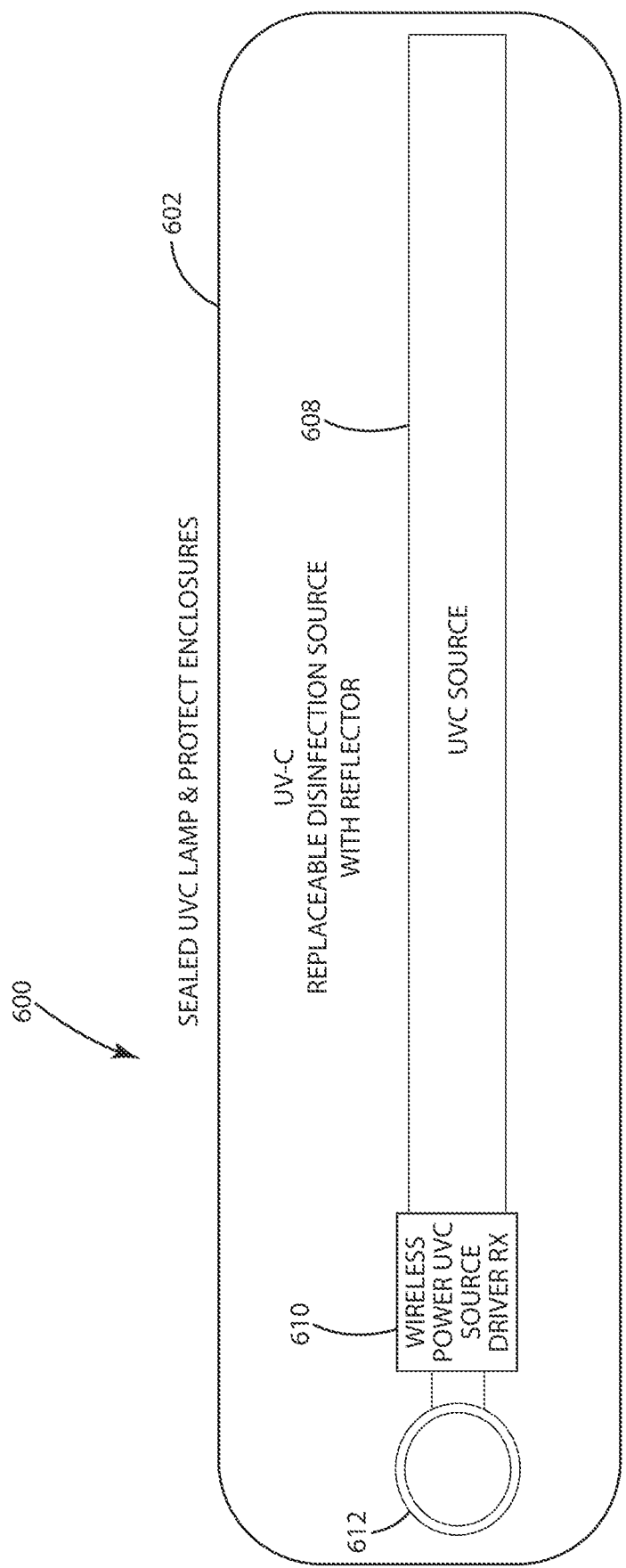
FIG. 6 illustrates a representative block diagram of another embodiment of a sealed UV lamp assembly.

FIG. 6 illustrates a sealed wirelessly operable UV lamp 600 configured for ease of replacement and controlled usage. In contrast to the sealed UV disinfection engine 500 of FIG. 5, the sealed wirelessly powerable UV lamp 600 of FIG. 6 is configured for external control. The depicted sealed UV lamp 600 generally has fewer components making it more cost-effective as a replaceable unit. The replaceable sealed wirelessly powerable UV lamp 600 of the depicted embodiment includes an enclosure 602 surrounding the electronics including a UV-C source 608, a combined wireless power receiver and UV-C source driver 610 and a wireless receiver coil 612. The enclosure 602 can act as a protective enclosure that prevents tampering and generally isolates the UV lamp components. The lamp 600 can include memory and a communication module, such as an RFID tag or other wireless communication system, for transmitting data, such as data relating to the lamp statistics, such as lamp life, lamp starts, and other lamp statistics. The RFID can also include authentication information that interacts with an authentication service in the equipment to which the UV lamp is installed to prevent lamp replacement with an unknown product.

Although the current embodiment does not include any sensors, sensors such as those discussed above in connection with the FIG. 5 sealed UV disinfection engine can be incorporated into UV lamp 600. The lamp 600 may include a controller and memory for controlling operation and collecting information from the sensors or alternatively the sensors may be configured to automatically communicate sensor output to a communication module in the UV lamp 600 for relaying to an external device.

The sealed UV lamp 600 can be configured with modular disinfection systems such that, when installed, the wireless power receiver coil 612 is aligned with a wireless power transmission coil in the corresponding equipment. Further, the enclosure 602 can be UV transmissive or UV transparent allowing UV-C energy to reach and be guided by any light guiding structures in the equipment or be configured such that, when installed, the UV-C energy from the lamp is directed toward the target disinfection area. The UV lamp 600 may optionally include a reflector. The reflector can be integrally formed as part of the enclosure 602, or can be installed on a portion of the inside or outside surface of the enclosure in order to reflect UV-C energy toward a certain path. The shape of the enclosure 602 and configuration of the internal components can vary from application to application. In some embodiments, the shape and size of the UV lamp 600 may be selected such that the lamp can be inserted into UV receiver slot in the equipment. The UV receiver slot and the UV lamp 600 can be physically configured and shaped to cooperate for aligning the various electronic components, for example aligning the wireless power receiving coil 612 in the lamp 600 with a wireless power transmission coil in the equipment. As another example, the physical configuration between the equipment and sealed UV lamp can include orienting and holding the sealed lamp 600 in place such that a reflector of the lamp 600 is positioned to reflect UV energy away from internal equipment components and instead toward a UV transmissive surface, UV transmissive aperture, or generally toward the target disinfection surfaces of the equipment.

Figure 7:
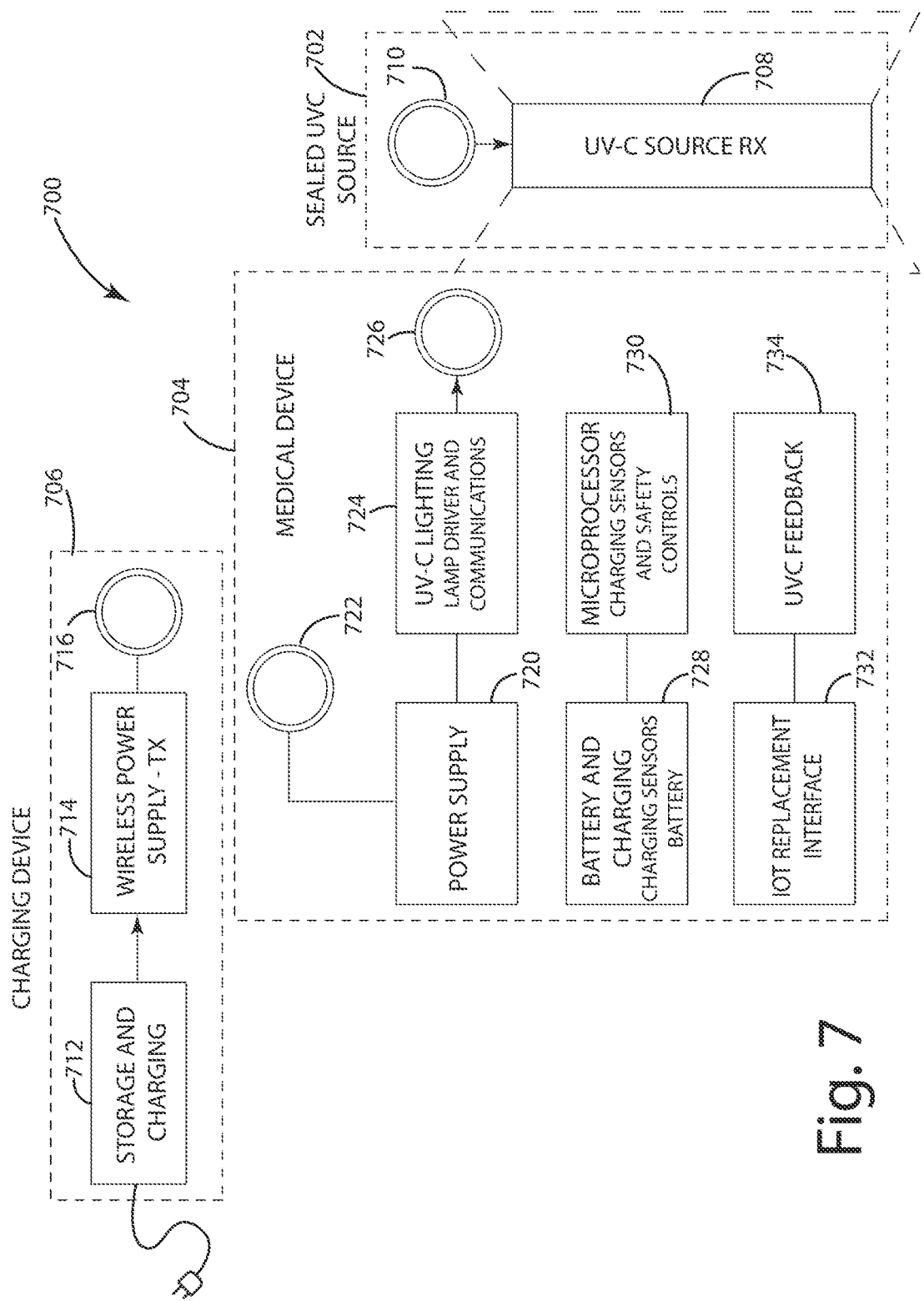
FIG. 7 illustrates a representative block diagram of a wireless power, medical device, and sealed UV lamp assembly equipment configuration.

The sealed UV lamp 600 of FIG. 6 can be utilized in a number of different configurations with a wide variety of applications. For example, FIG. 7 shows an equipment configuration 700 that includes a wall powered wirelessly power supply 706 that both charges a medical device 704 and also powers a sealed UV-C source 702 to disinfect the medical device 704. In this configuration, the medical device can docked, set on, or moved in proximity to the wireless charging device 706 to align the charging device's wireless power transmitter primary 716 with the medical device's wireless power receiver secondary 722. The power supply can include storage and charging electronics 712 that interact with a wireless power supply transmitter unit 714 to wirelessly supply inductive energy from the transmitter primary 716, for example by applying VAC across the coil. The medical device can receive the inductive energy at the receiver coil 722, which can be converted at its power supply 720 to power and charge the various components on the medical device, including, for example, the battery and charging system 728, the microprocessor 730, the IOT replacement interface, the UV-C feedback components, and the UV-C lighting components. The UV-C lighting components can include a UV lamp driver and communication module, such as an RFID reader for communicating with the sealed UVC source 702 and a wireless communication system for communicating to a device over the Internet or local network. Thus, the charging device 706 can both power and charge the medical device. The wireless power coil 726 coupled to the UV-C lighting lamp driver is energized based on output from the microprocessor, which accepts input from various sensors and includes safety controls as well as the logic for any disinfection model or disinfection method that controls the timing of the UV-C energy output by the sealed UVC source 702. The sealed lamp 702 can receive power wirelessly as depicted, or alternatively, the lamp may be wired to the UV driver of the medical device, for example using connectors or contacts. Further, the sealed UV source is shown as a separate block diagram outside of the medical device for ease of description, but it should be understood, the sealed UV source 702 can be configured to be received by a UV sealed lamp receiver compartment, such as a slot, that holds the UV lamp 702 in place to provide UV-C energy that disinfects the touch surfaces of the medical device. For example, in one embodiment, the UV lamp can be inserted in the handle of a scanner device, as discussed in connection with FIG. 9. In another embodiment, the UV lamp can be utilized in connection with a medical cart similar to the one shown in FIG. 3, where the medical cart is adapted such that some of the electronics of the FIG. 5 sealed disinfecting medical device protective enclosure are installed on the medical cart, instead of within the sealed lamp. In another example, one or more sealed UV lamps can be inserted into a vacuum as discussed in connection with FIGS. 14-15. Further, the sealed UV lamp can be utilized in connection with drawer embodiments (e.g., FIGS. 16-17 and 19) as well as cabinet embodiments (e.g., FIG. 20).

In the depicted embodiment, the wireless receiver coil 722 and wireless transmitter coil for the sealed UV lamp 726 are separate, which enables the system to easily be charged and disinfected simultaneously. The UV-C lamp 702 may be configured such that it disinfects not only the medical device, but also target disinfection areas associated with the charging device 706. Further, in some alternative embodiments, the wireless receiver secondary coil 722 and the wireless transmitter primary coil 726 may be a single coil that can be configured to both receive power from the charging device 706 when proximate the charging device and transmit power to the sealed UV-C 702 source when proximate to receiver coil 710. Further, in such a configuration to enable simultaneous charging and disinfection, the wireless power transmitter coil 716 maybe simultaneously aligned with the medical device receiver coil 722 and the sealed UV source coil, and transmit power to both the medical equipment 704 and the UV source 702 simultaneously.

Figure 8:
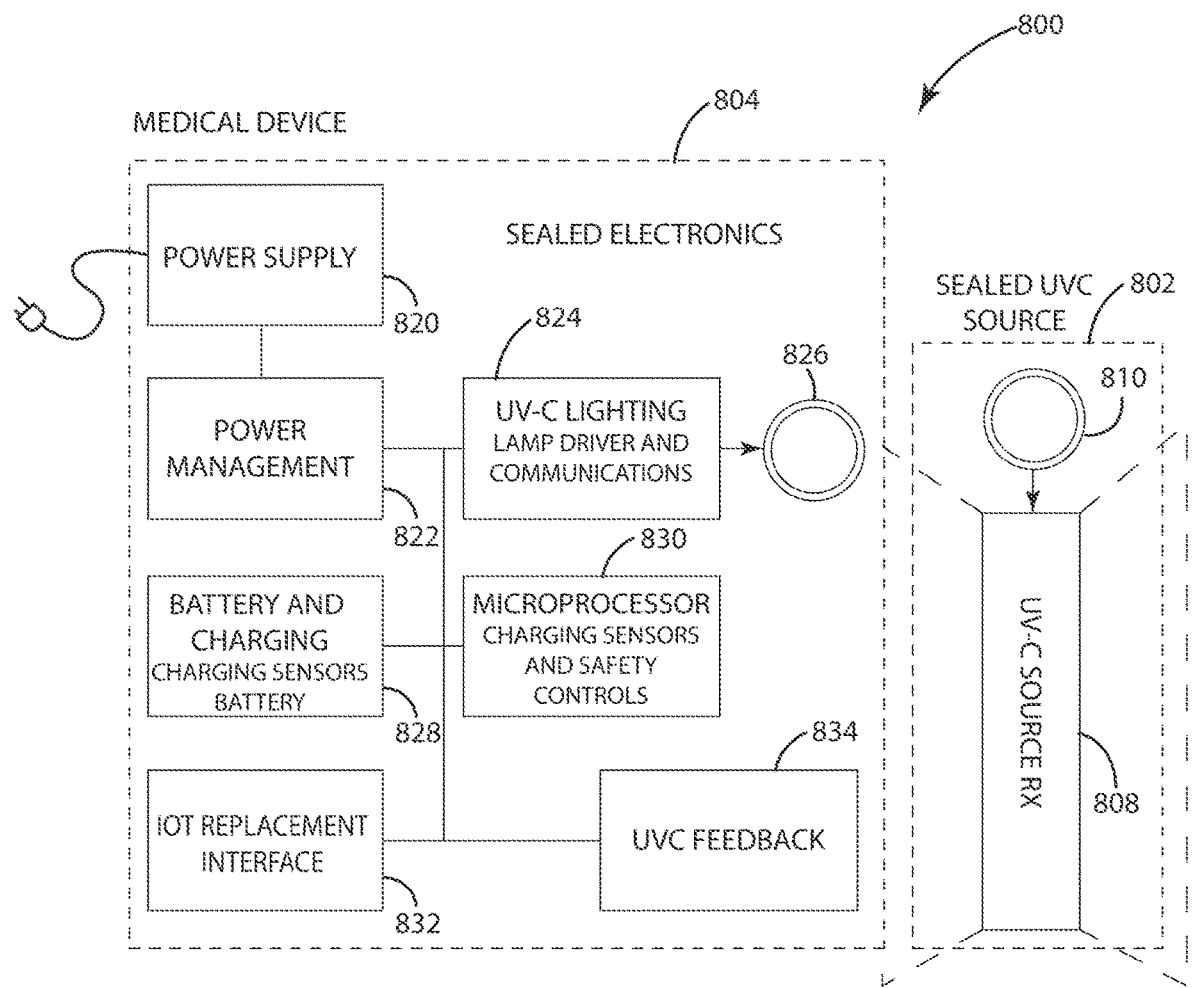
FIG. 8 illustrates a representative block diagram of a sealed medical device and sealed UV lamp assembly equipment configuration.

FIG. 8 shows another equipment configuration 800 similar to that of the equipment configuration of FIG. 7, the primary difference being that the medical device 804 plugs directly into a wall socket as opposed to receiving wireless power from a wireless charging unit.

Figure 2:
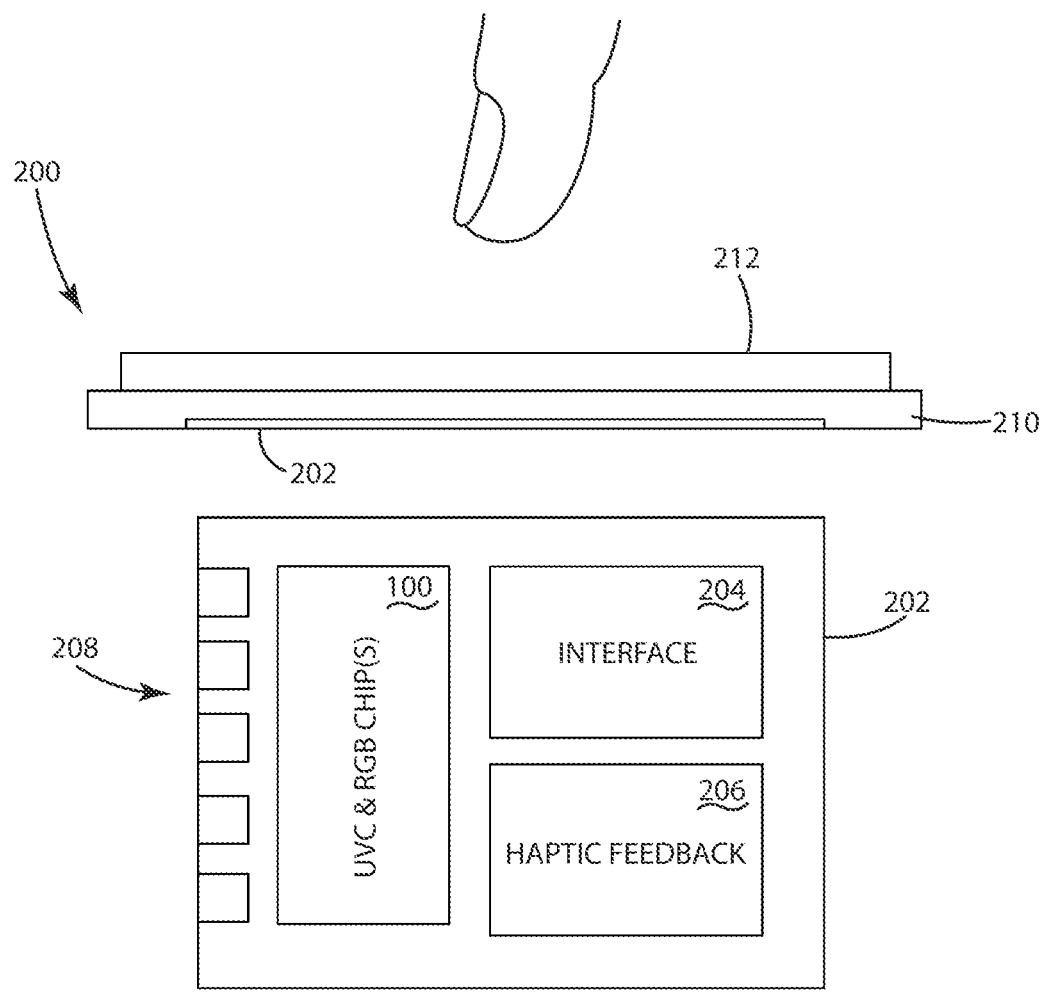
FIG. 2 illustrates a representative block diagram and sectional side view of a UV-C touch and feedback user interface module.
Figure 9:
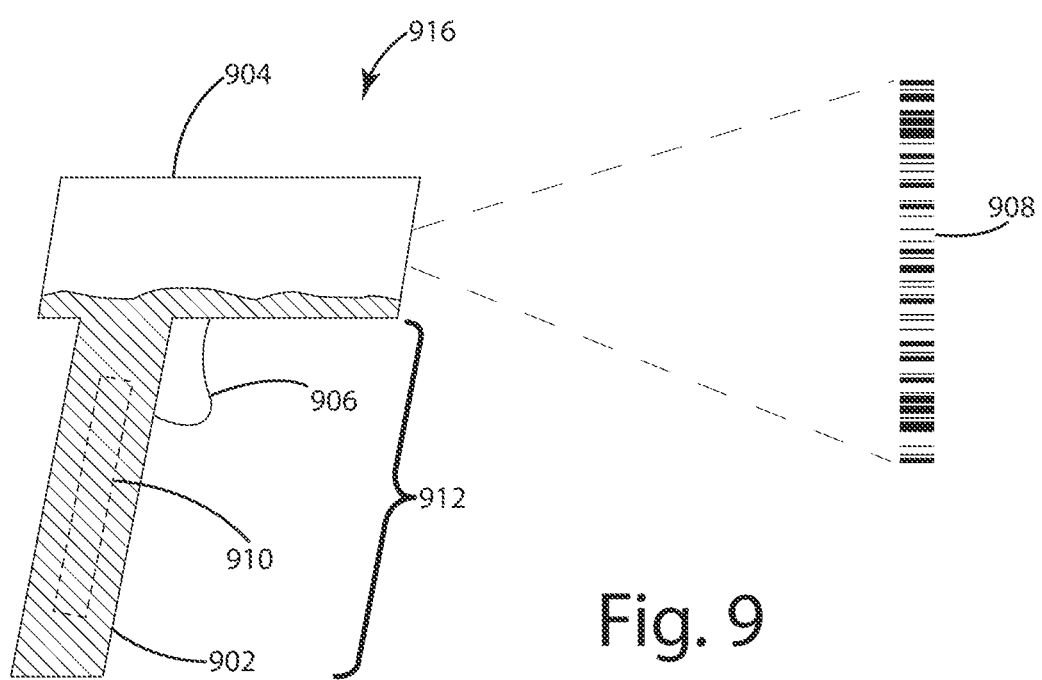
FIG. 9 illustrates a side view of a scanner having an internal UV source.

FIG. 9 illustrates a scanner with an internal UV source 910 that projects a UV pattern 912 on a transmissive material for disinfection. The internal UV source 910 can be, for example, any of the sealed disinfecting medical device protective enclosure of FIG. 5, the UVC touch & feedback user interface module of FIG. 2, the human machine interface and disinfection integrated circuit of FIG. 1, the sealed UV lamp and protective enclosure of FIG. 6 or FIG. 18. Referring to FIG. 9, the depicted scanner 916 is a hand-held barcode scanner typical of the kind used within a healthcare environment to scan barcodes 908, for example during medical record entry. The scanner 916 includes a scanner head 904 coupled to a scanner handle 902, and a trigger 906 for activating the scanner. The handle 902 can be manufactured or coated with a UV transmissive material to assist in UV-C energy distribution from the internal UV source 910 to the external contact surfaces in the areas shown by the UV pattern 912. In alternative embodiments, the internal UV source and UV transmissive materials can be configured to provide effective UV disinfection to the entire exposed surface of the scanner 916. Although FIG. 9 is described and illustrated in connection with a scanner having an internal UV source, it should be recognized that the scanner is merely one example of equipment that can be utilized in connection with embodiments of the present disclosure. The configuration and construction is applicable to other types and forms of equipment, such as other medical equipment, office equipment, automotive equipment, automated teller machines, and mobile equipment, to name a few.

Figure 10:
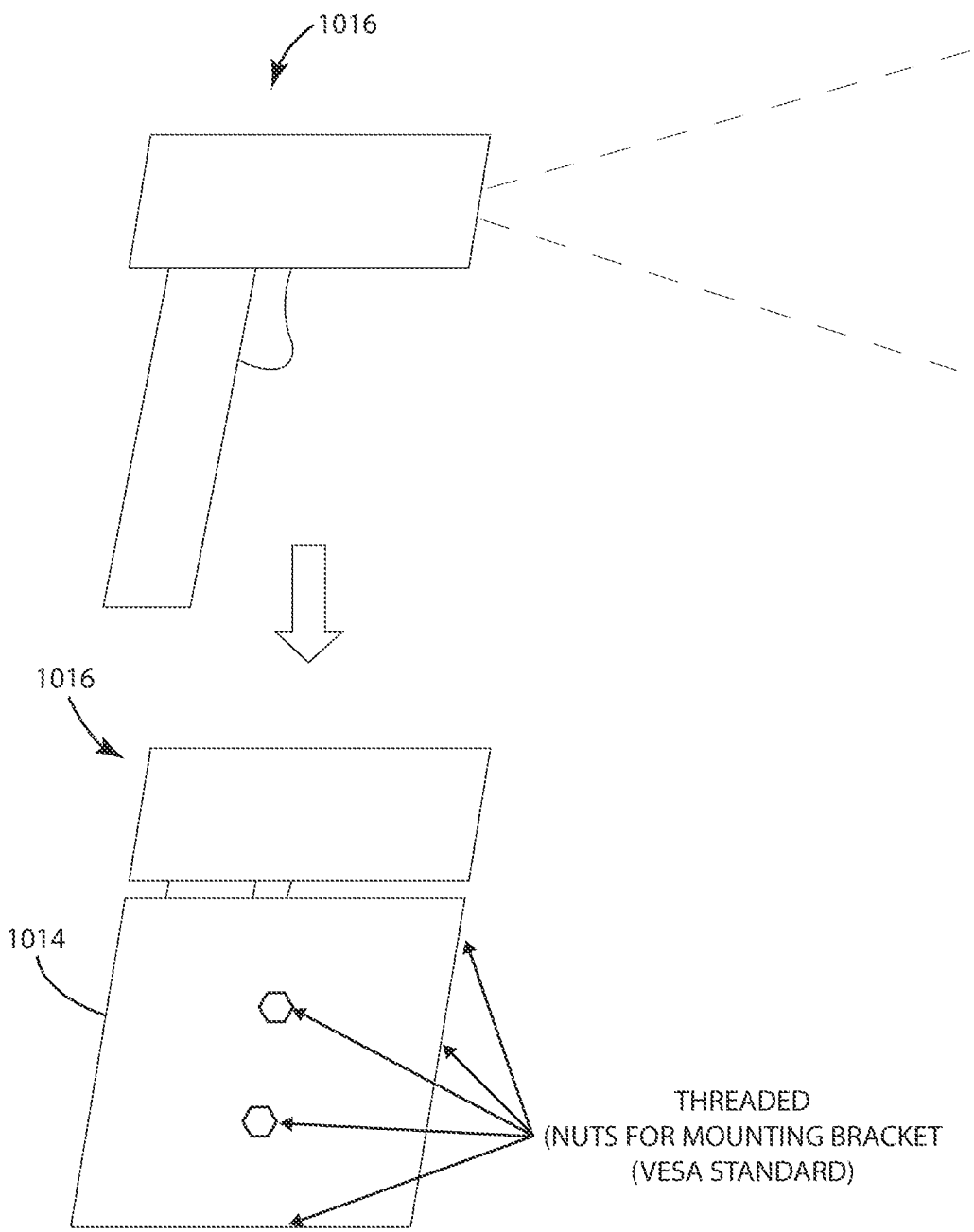
FIG. 10 illustrates insertion of a scanner into a holder for UV disinfection.

FIG. 10 illustrates a scanner holder 1014 that has UV disinfecting capability. The conventional scanner 1014 can be disinfected while placed in the holder 1014 for storage between uses. The holder 1014 can be mounted to other equipment or free-standing equipment. For example, the holder 1014 can be mountable according to the VESA standard, for example, adjacent a monitor or on a medical cart. The holder can include a UV source for directing UV-C light to the target disinfection area, e.g., handle of the scanner. Alternatively, the holder can have a UV light passage for receiving UV-C light from another device having a UV source, e.g., the holder 1014 can be installed onto a medical cart or other equipment such that the UV light passage aligns with a UV window in the equipment.

Figure 11:
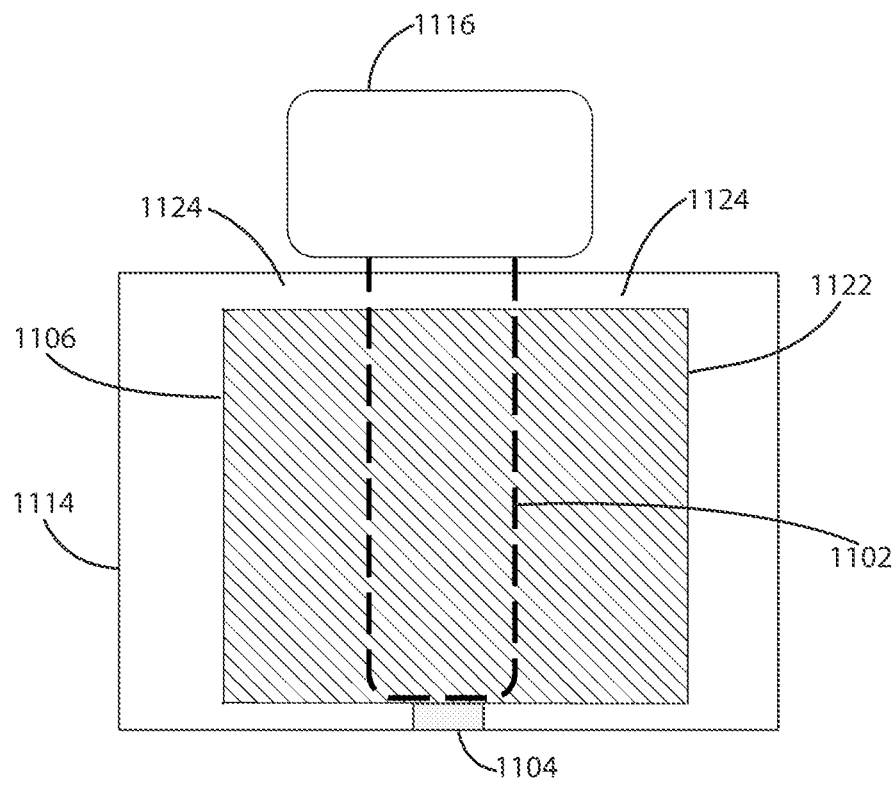
FIG. 11 illustrates a rear view of a wired scanner and holder.
Figure 12:
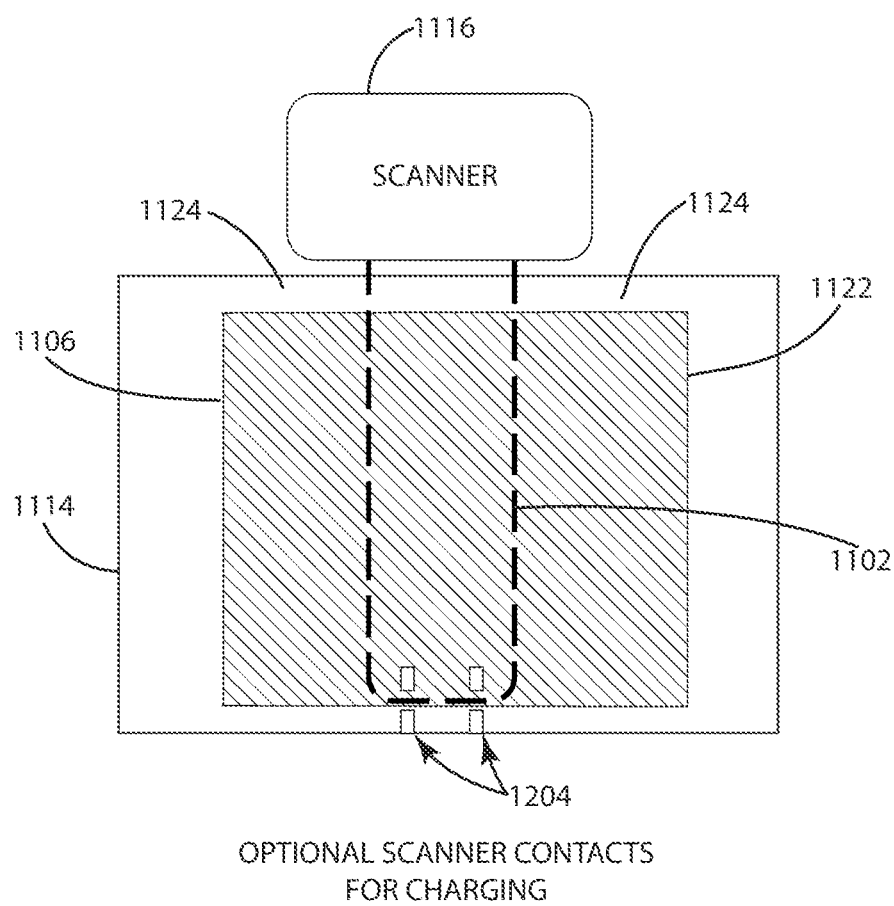
FIG. 12 illustrates a rear view of a wireless scanner and holder.

FIG. 11 depicts a rear access view of one embodiment of the FIG. 10 holder. The holder 1114 can be mounted to equipment such that the internal disinfecting chamber 1106 receives UV light from the equipment. The chamber 1106 can include a reflective surface 1122 for reflecting UV light in the chamber to disinfect the scanner handle 1102 inserted in the holder. The holder 1114 can include an area of the chamber without a reflective coating where portions of the holder 1124 are UV transmissive for disinfecting the bottom portion of the head of the scanner 1116. Accordingly, the storage cradle can include materials that are lighted with UV light. The materials can be selected and the UV source operated to ensure that UV light is transmit out of the UV transmissive holder with a low intensity that is innocuous. That is, a control system can ensure the UV light is operated during periods without human presence, deactivates in the presence of humans, and to the extent that the system is activated during human presence, that the UV-C dosage is small such that no human is exposed to UV-C energy for a prolonged period of time. FIG. 11 shows the holder with a port for cord access for the scanner, while FIG. 12 depicts another embodiment with optical scanner contacts 1204 for charging. Presence of the contacts does not limit wireless charging options.

Figure 13:
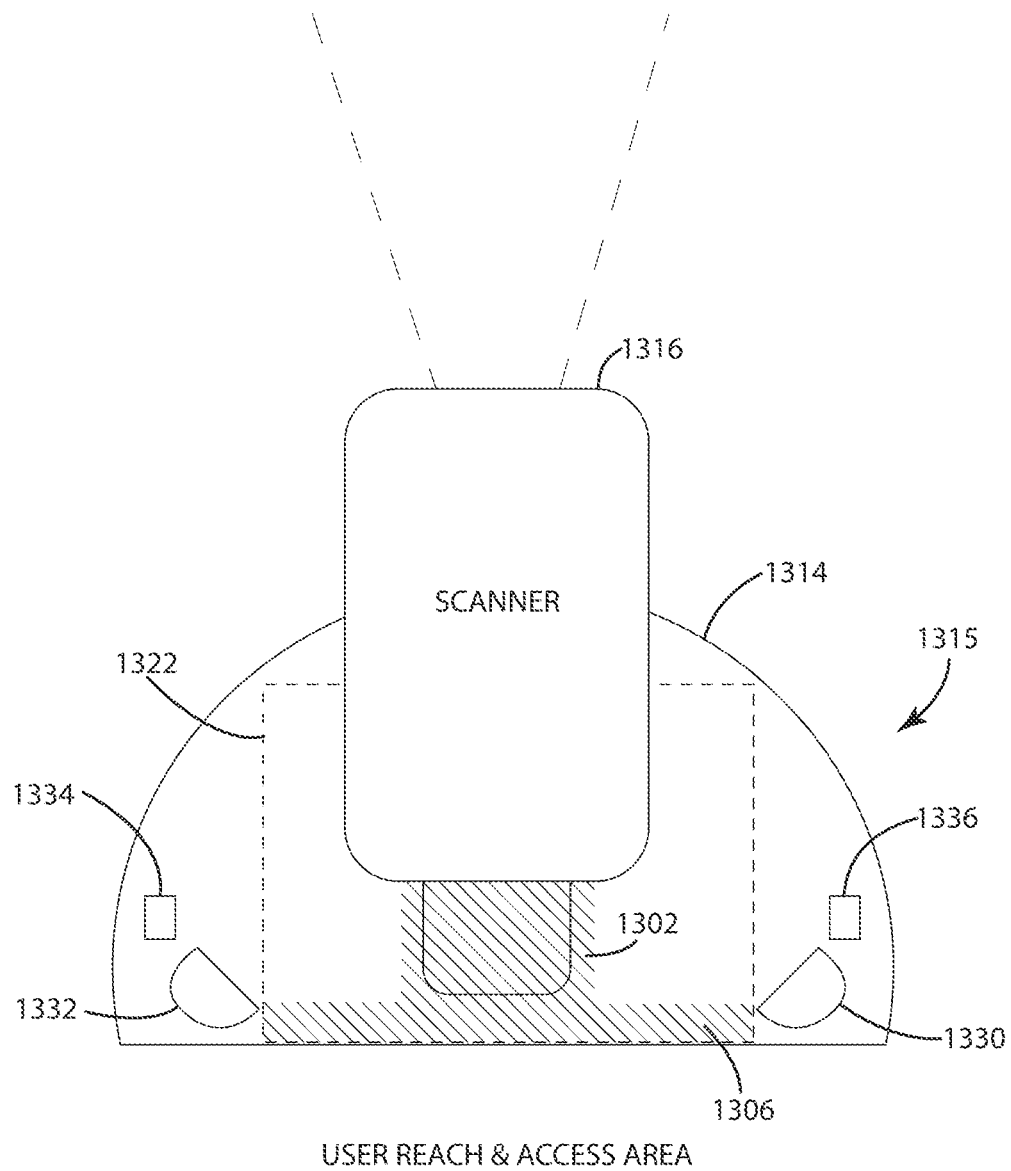
FIG. 13 illustrates a top view of a scanner and cradle with disinfection capabilities.

FIG. 13 depicts another embodiment of a scanner 1316 and cradle 1315, which depicts an example of the light patterns 1302, 1306 and cradle position in order to treat the scanner effectively while allowing easy human interface. The UV lamps 1332, 1330 coordinate to provide UV-C energy to the cradle 1315. In the top view, the upper UV transmissive bracket 1322 is depicted in broken line and the UV pattern 1302, 1306 shows how the UV transmissive bracket 1322 contributes to disinfecting the bottom surface of the scanner 1316 head. The cradle can include sensors, such as motion sensors 1334, 1336 that can detect user proximity when users reach and access the handle of the scanner such that the UV-C sources can be deactivated in response either according to a control system (not depicted) or via an automatic shut off with the UV sources. The inner surface 1314 of the cradle can be reflective, such as via a UV reflective coating or UV reflective material.

Figure 14:
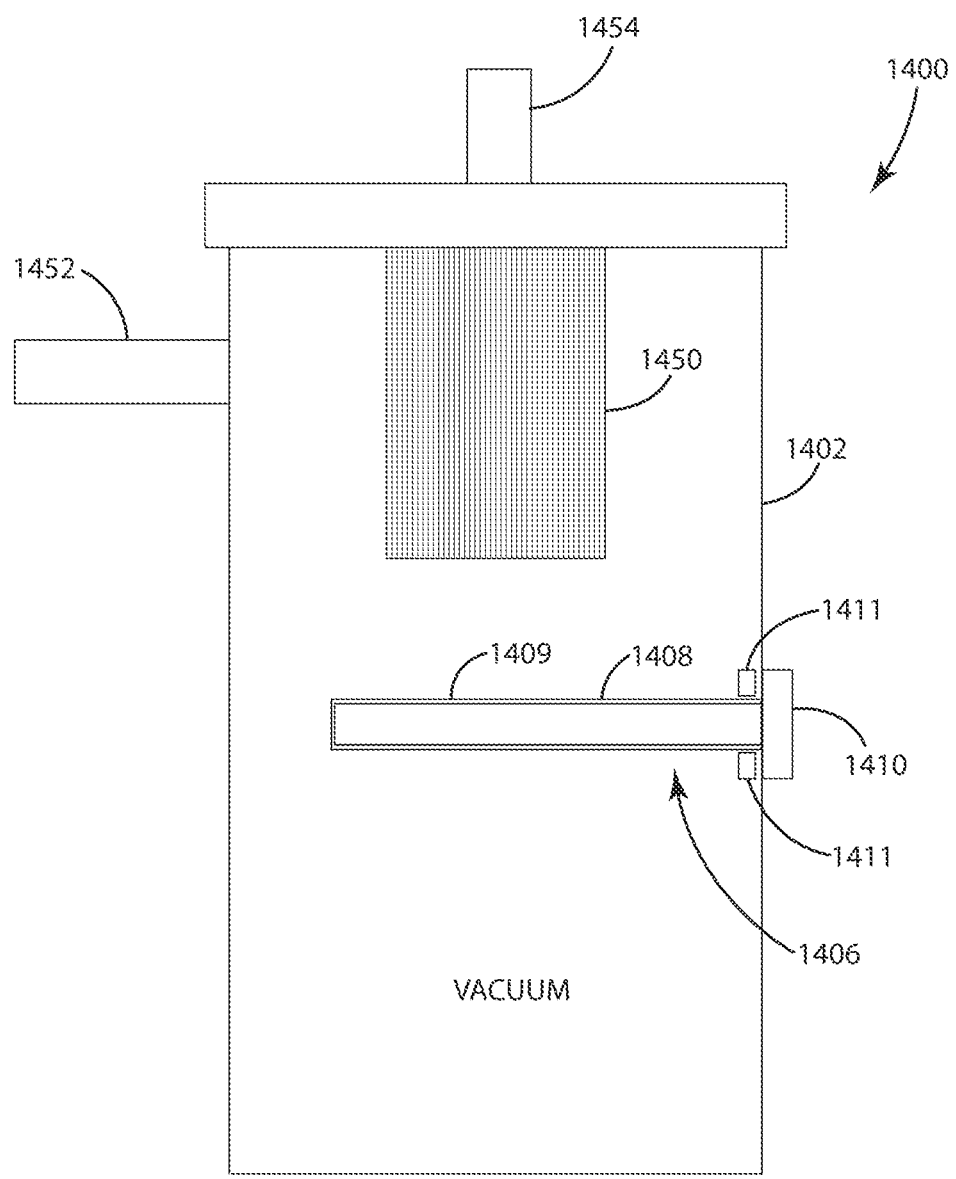
FIG. 14 illustrates a vacuum with a compartment for receiving a sealed UV lamp assembly.

FIG. 14 illustrates UV treatment of a vacuum canister. UV sensors can be utilized to determine proper UV dosages while running and between uses. FIG. 14 is s a sectional view of a vacuum canister 1400 that includes a housing 1402, a filter 1450, an inlet hose 1452, and an outlet hose or vent 1454. The vacuum includes a compartment for receiving a replaceable sealed UV lamp 1406, depicted in FIG. 14 fully installed within the compartment of the housing 1402. Specifically, the sealed UV lamp 1406 is received by a slot 1409 that includes physical retention features such that the sealed UV lamp 1406 is held or locked in place when fully inserted and such that the UV-C energy from the lamp 1406 is positioned to distribute UV-C energy throughout the vacuum canister to target disinfection areas in such position. The sealed UV lamp 1406 can be positioned such that when seated in the slot 1409 it receives power from the vacuum, for example by virtue of electrical contacts between the replaceable UV lamp and the vacuum.

In one embodiment, the lamp driver control, RFID and feedback are integrated into a movable cover 1410 for the slot 1409. The cover 1410 can be slid or rotated to provide access to the slot 1409 for inserting the sealed UV lamp 1408 in the housing 1402. Once the sealed UV lamp 1408 is installed, the movable cover 1410 can be moved to cover the slot 1409 to aid in retaining and powering the lamp 1409. For example by virtue of electrical contacts in the cover 1410 interfacing electrical contacts on the sealed lamp 1409 or wireless power transmission from the vacuum with a transmitter coil in the cover 1410, to a wireless power receiver coil in the UV lamp assembly 1408. The UV lamp 1408 and cover 1410 may include an RFID tag and reader, respectively, for communication.

Figure 18:
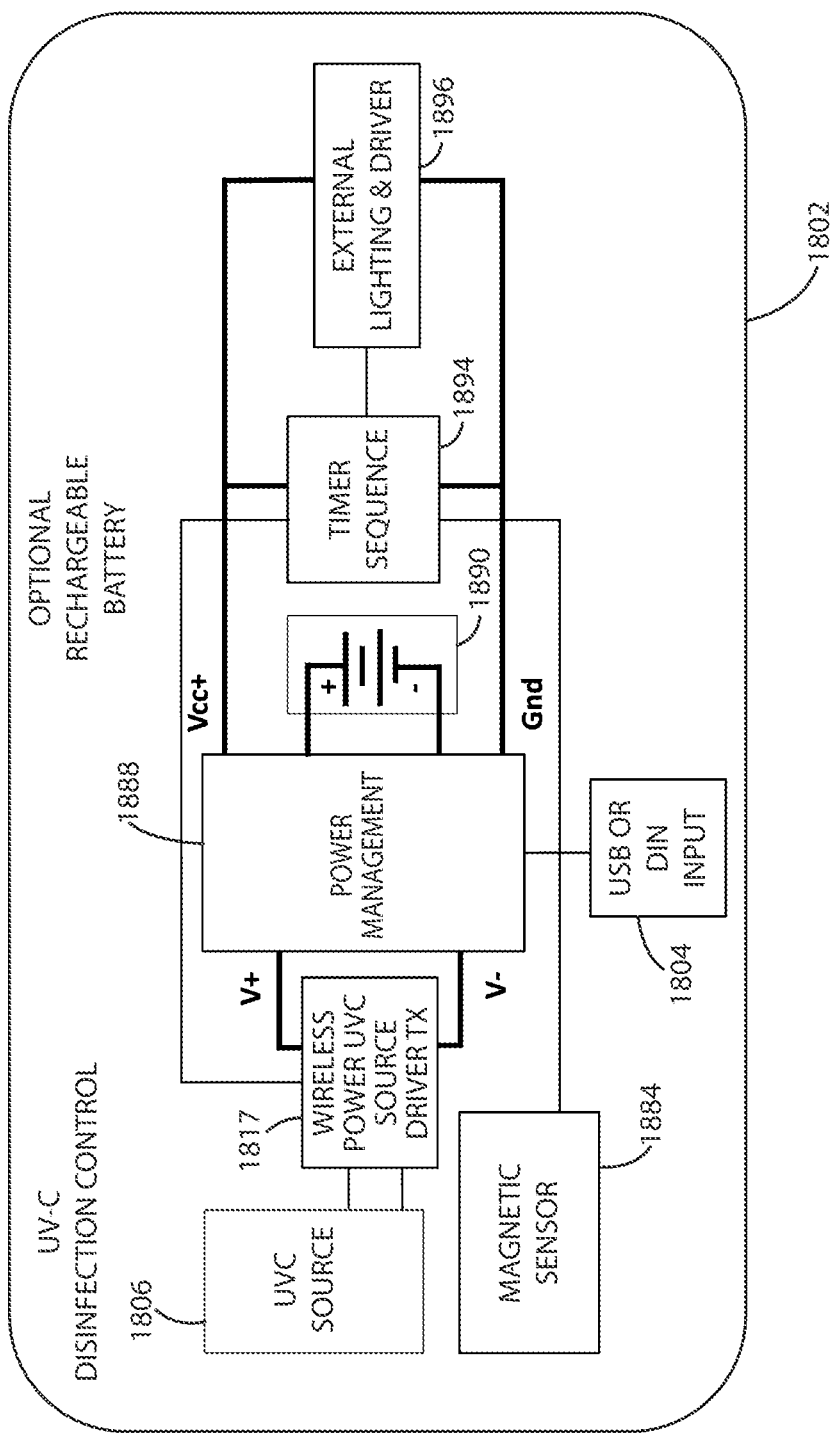
FIG. 18 illustrates a representative block diagram of an embodiment of a UV disinfection control enclosure.

In an alternative embodiment, the sealed UV lamp 1408 can include electronics 1410, for example in the configuration depicted in FIG. 6, FIG. 18, or elsewhere in the disclosure. In this alternative embodiment, the sealed UV lamp 1408 can be inserted into slot 1409 and by virtue of full insertion and engagement, the UV lamp 1408 can be held in place, and aligned with an electronics module 1411 that includes wireless power coil or electrical contacts in the vacuum for transferring power to the sealed UV lamp 1408. The module 1411 may also include control circuitry to control operation of the sealed UV lamp.

Figure 15:
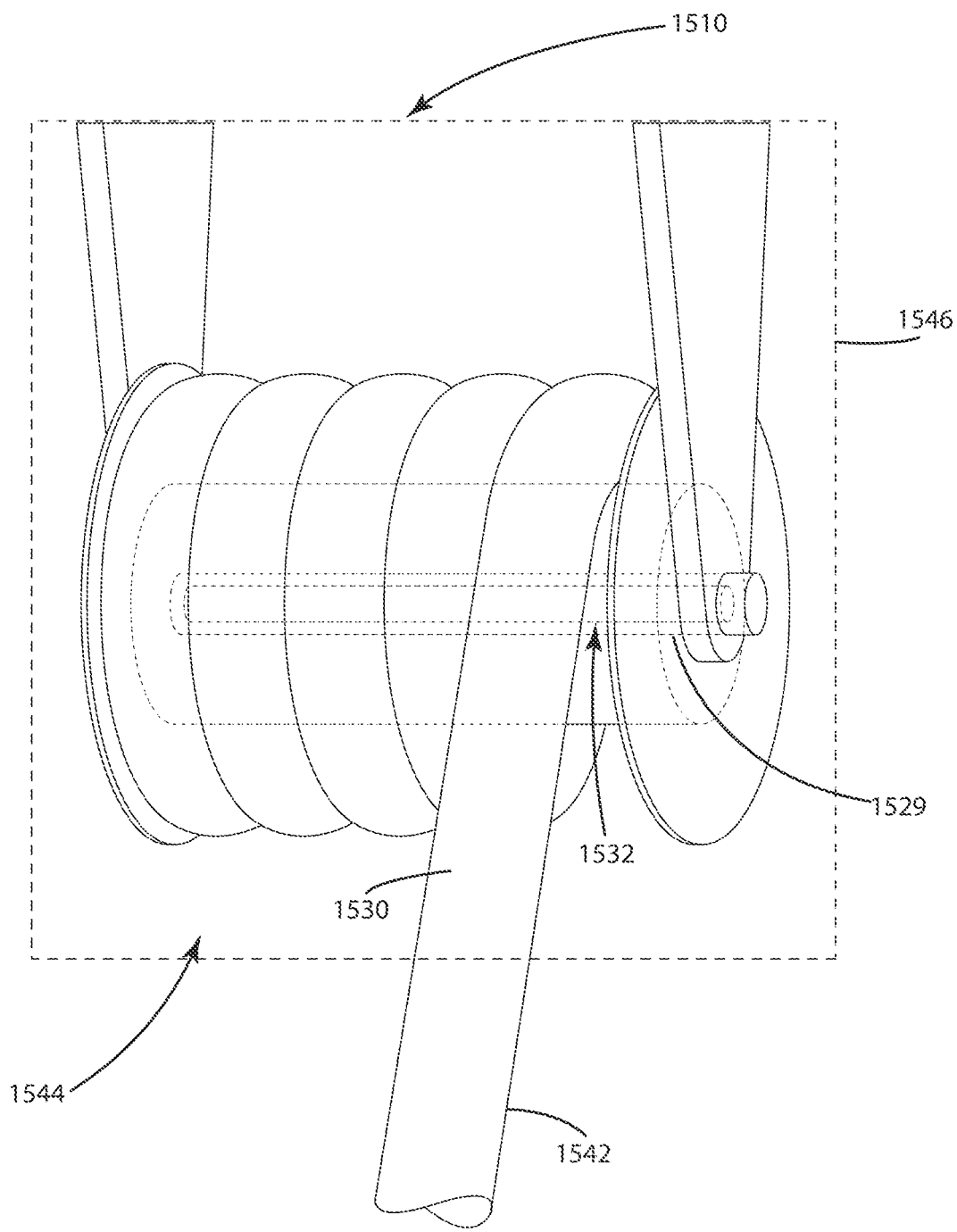
FIG. 15 illustrates a vacuum with multiple compartments for receiving a sealed UV lamp assembly.

FIG. 15 depicts a hose winding system and treatment method for disinfecting hoses that are drug across floors and pick up unwanted biologicals. In the depicted partial view of a vacuum embodiment, multiple sealed UV lamp assemblies can be installed into the vacuum. Alternatively, one sealed UV lamp assembly can be utilized in connection with the vacuum and moved between two positions depending on the target disinfection area. For example, the sealed lamp 1532 can be installed within a compartment 1529 of a UVC transmissive drum 1530 such that the vacuum hose 1542 wound around the drum 1530 can be disinfected. The housing surrounding the drum can include a UV reflective inner lining 1544. Another UV lamp assembly 1509 (or the UV lamp assembly 1532 can be moved) to another sealed UV lamp slot to provide disinfection of another area of the vacuum.

Although FIGS. 14-15 are described and illustrated in connection with a vacuum that receives a sealed UV lamp, it should be recognized that a vacuum is merely one example of equipment that can be utilized in connection with embodiments of the present disclosure. The configuration and construction is applicable to other types and forms of equipment, such as medical equipment, office equipment, cleaning equipment, automotive equipment, automated teller machines, and mobile equipment, to name a few.

Figure 16:
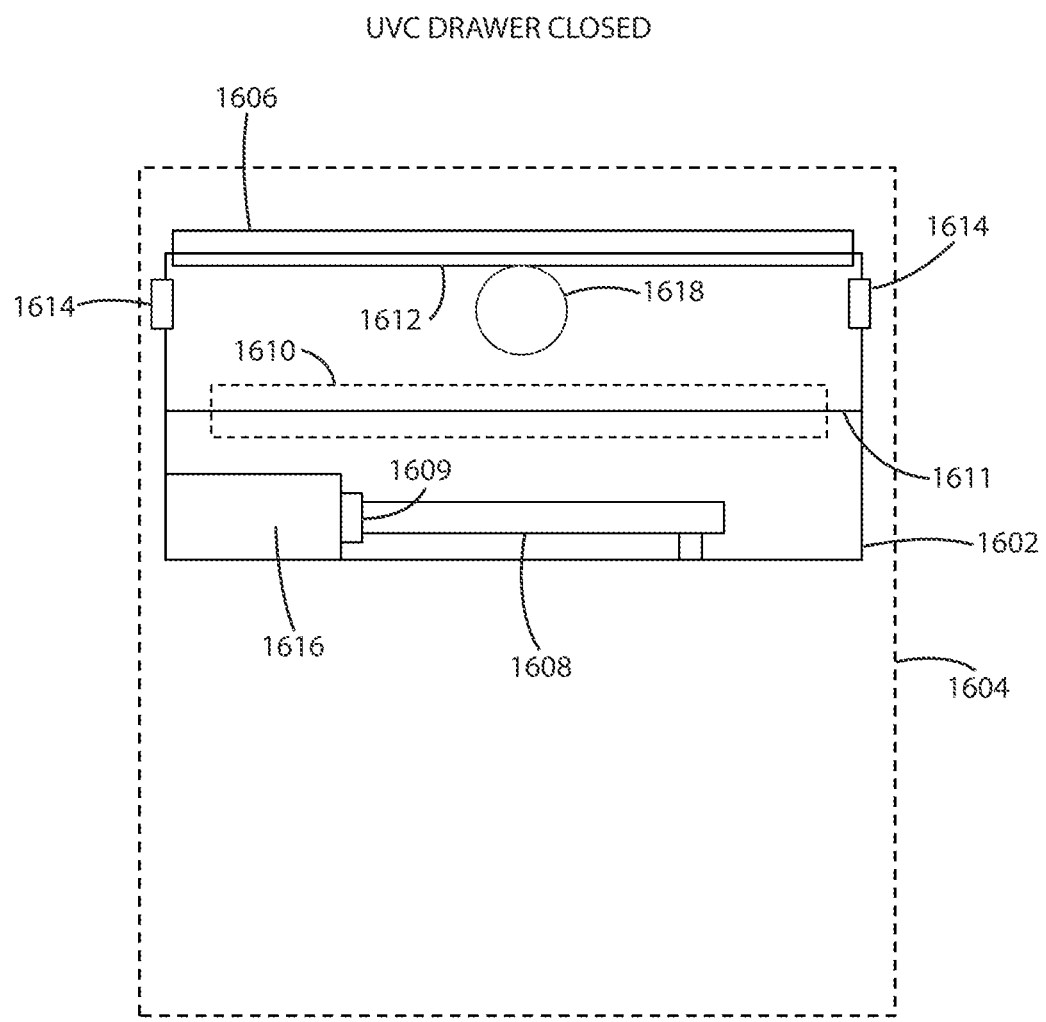
FIG. 16 illustrates a representative side sectional view of a UV disinfection drawer with wireless power interlock in a closed configuration.
Figure 17:
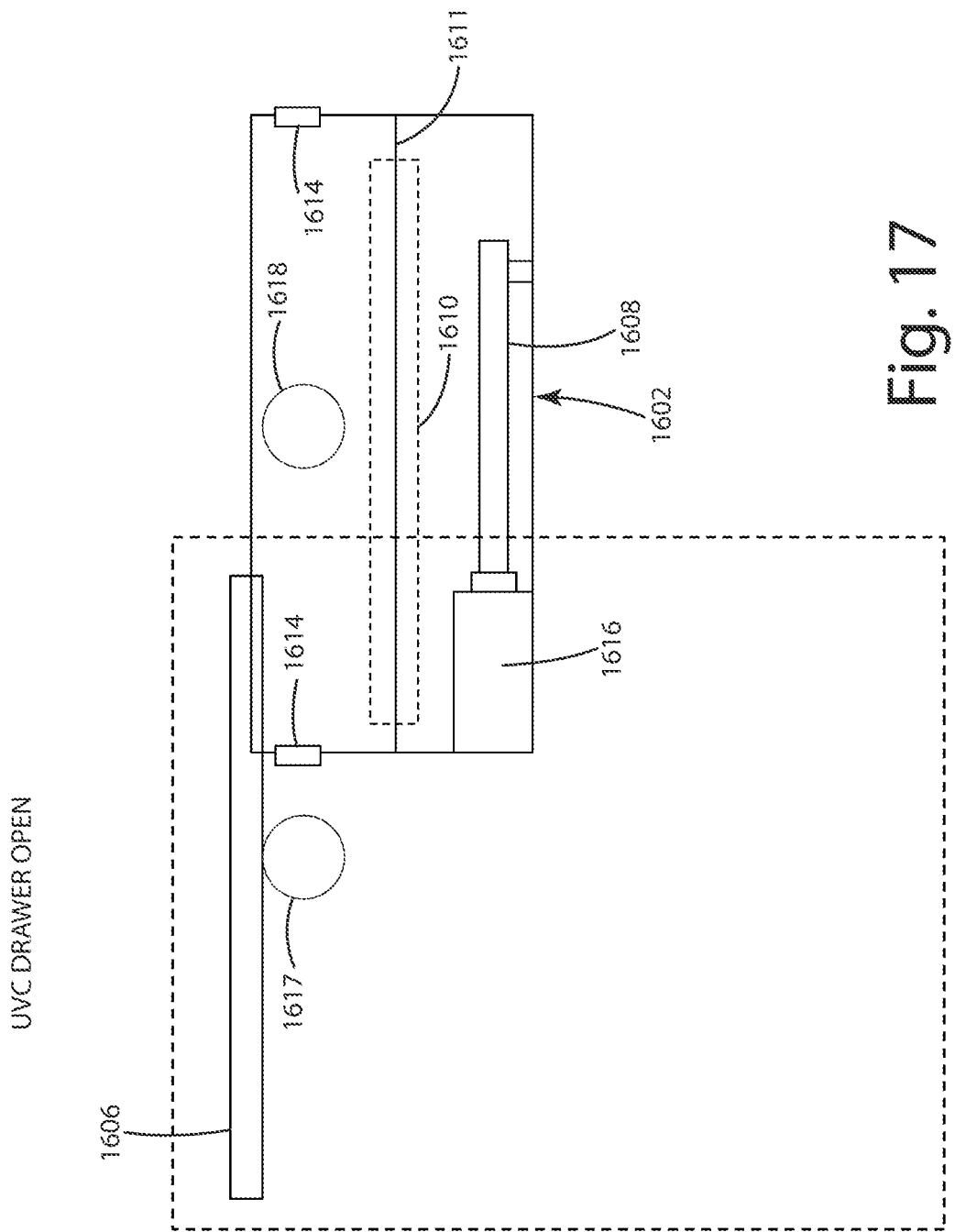
FIG. 17 illustrates a representative side sectional view of a UV disinfection drawer with wireless power interlock in an open configuration.

FIGS. 16-17 illustrate sectional views of a drawer system in a closed and open configuration, respectively. FIG. 16 shows a cabinet 1604 having a drawer 1602 in a closed configuration where wireless power Tx and Rx coils 1618 align to enable power flow. This powers the electronics 1609 and UV source 1608, which are electrically coupled to the Rx coil 1618 through wires that are organized, in part, by the wire cover 1616. The UV source can be a UV LED, low pressure Hg, cold cathode, or another variation of UV source. The electronics 1609 can include timers, a state machine or microprocessor, among other electronics. The drawer can include a UV transmissive tray 1611 for holding parts in place for disinfection. The tray can include features to orient objects 1610, such as vacuum tools, placed in the tray in a proper orientation. The UV transmissive material of the tray can also assist in ensuring disinfection of items in the tray. In addition, a reflective surface can be installed between, just below, or just above the slide rails 1606 that reflects UV light to increase disinfection effectiveness of items in the tray 1610. The parts themselves may be made of transmissive materials. The drawer may include a UV-C window that converts UV energy into visible light. Accordingly, during activation of the UV light in the closed drawer configuration, the visible light from the UV window is indicative of ongoing disinfection.

FIG. 17 shows the drawer 1602 in the open position. The coils are separated due to the drawer being pulled out causing the receiver coil to move out of proximity of the transmitter coil 1617. This movement of the coils as a result of moving the drawer acts as a power interlock. That is, the drawer being pulled apart from the cabinet causes power stops flowing to the electronics 1616 and UV source 1608. The driver and electronics for the wireless power link can be mounted to an upper bracket.

In operation, the cabinet 1604 is a stationary support structure including a wireless power transmitter having an inductive primary, and the drawer 1602 includes a wireless power receiver having an inductive secondary where the wireless power receiver electrically coupled to a UV treatment device. The drawer slides 1606 are two-way drawer slides with a stop. Each drawer slide includes a cabinet profile that attaches to the cabinet and a drawer profile that attaches to the drawer and slides with respect to the cabinet profile. The drawer is slidably configurable via the drawer slides between a closed configuration where the wireless power transmitter and the wireless power receiver are aligned to form a wireless power link for supplying power to the UV treatment device and an open configuration where the wireless power transmitter and the wireless power receiver are unaligned such that the wireless power link is broken automatically halting any supply of power to the UV treatment device. The wireless power link acts as both a ballast and a safety interlock. The control circuit in the electronics 1609 can be configured to delay activation of the UV treatment device 1608 in response to the drawer configuration changing to the closed configuration forming the wireless power link. Further, the UV reflective surface 1612 disposed proximal the pair of drawer slides 1606 can be configured such that UV energy output by the UV treatment device 1608 reflects off the UV reflective surface 1612 and is sealed within the drawer 1604, or within the cabinet 1604 in the closed configuration.

The two-way drawer slides enable the drawer to open in two directions. For example, there can be two open configurations, a first open configuration resulting from slidably moving the drawer from the closed configuration in a first direction and a second open configuration resulting from slidably moving the drawer from the closed configuration in a second direction, opposite the first direction. In alternative constructions the drawer slides can be configured or located in a different position. Further, the drawer may move between the open and closed configuration without the use of drawer slides.

FIG. 18 shows an embodiment of an enclosed disinfection device and protective enclosure 1802. The control system depicted has a reduced number of features relative to the FIG. 5 embodiment. For example, the sealed UV lamp 1802 includes fewer control and communication features, which enables the unit 1802 to be manufactured and assembled at a lower cost. The depicted embodiment does not include a microprocessor, but instead uses a timer sequence circuit 1894 or state machine for controlling the other components. That is, a magnetic sensor or magnetic switch 1884, or other sensor/switch, can be used to trigger various timing sequences in the timer sequence circuit 1894. The timers can be configured to activate the UV source after a delay by controlling the UV source via the driver 1817. That is, instead of immediately running a disinfection cycle, the timer sequence can include a waiting period after the magnetic sensor determines a magnet is in proximity, then after the waiting period the timer sequence can initiate a UV dose in a disinfection cycle by controlling the UV driver 1817. The timer sequence can also activate a general lighting cycle with the external lighting an driver module 1896 when the magnetic sensor stops sensing a magnet. The unit 1802 can include a battery 1890 to power the various electronic components or alternatively it may include a wireless power receiver. The unit 1802 may also include a USB, DIN, or other connector for accepting input.

Figure 19:
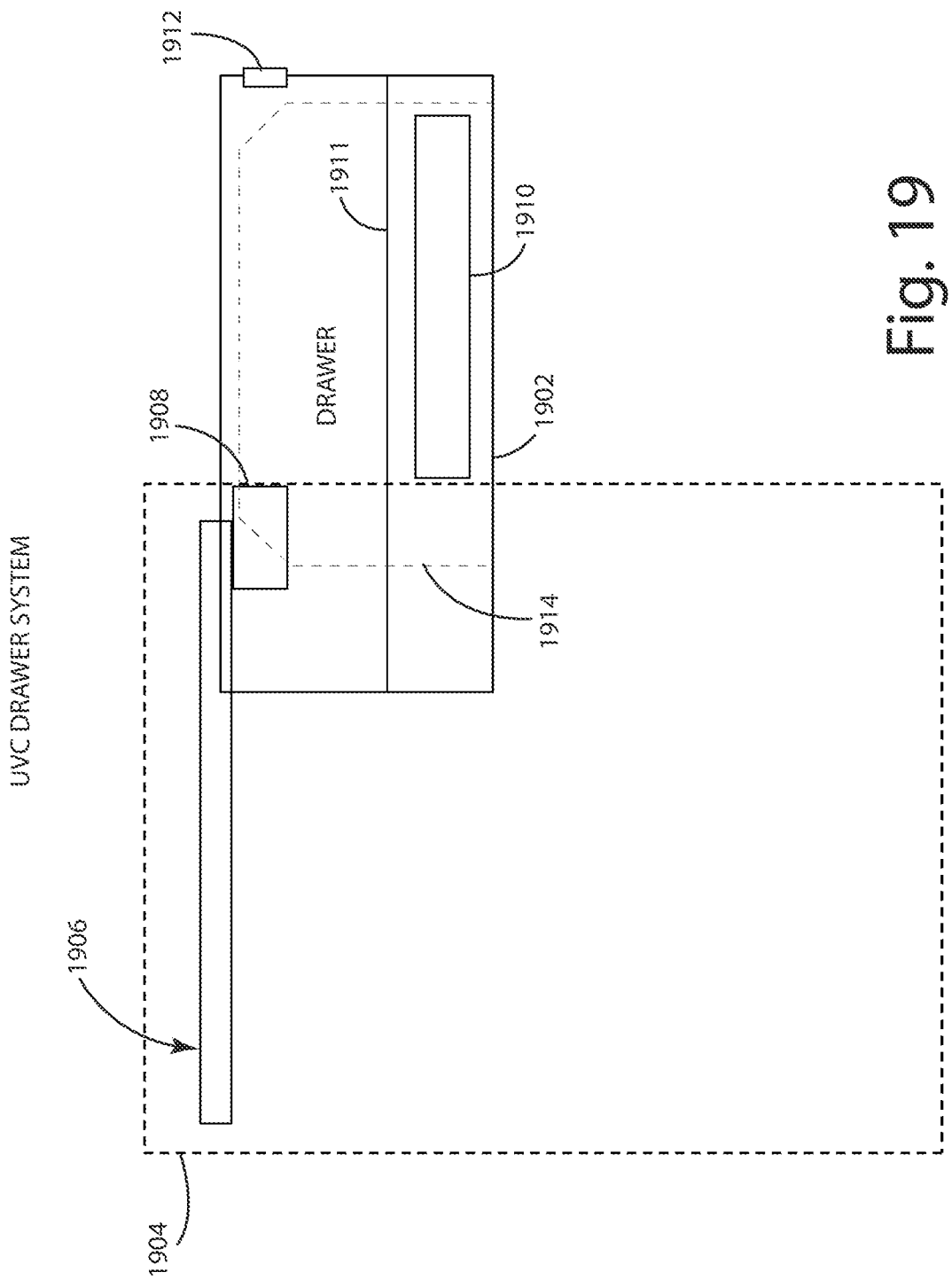
FIG. 19 illustrates a representative side sectional view of a UV disinfection drawer with magnetic interlock in an open configuration.

FIG. 19 illustrates another drawer embodiment. The cabinet 1904 includes a drawer treatment and lighting system 1908 where when the draw opens general, visible light RGB LED lighting lights the inside of the drawer, and when closed the control circuit waits a predetermined amount of time, e.g. 10 seconds, and then begins a UV disinfection cycle to treat the interior of the drawer for a predetermined amount of time, e.g. about 6 minutes. The drawer can include an optional UV transmissive tray 1911 and a combined UV source mobile wireless charger 1910 below the UV transmissive tray to assist in both charging and disinfecting devices, such as a mobile phone in 360 degrees.

The UV-C and lighting unit with a magnetic interlock 1908 can mount to the cabinet, for example to a cabinet support located proximate to the drawer slides 1906. The unit 1908 can include a wired power connection routed through the cabinet to a wall power outlet, for example located behind the cabinet. When the drawer is closed, the magnet 1912 installed near the face of the drawer interacts with a magnet in the unit 1908. The magnets can be installed with opposite poles facing each other. Further, the magnetics can form an electrical path from the unit 1908 that provides power to equipment in the drawer 1902. For example, power can be routed from the wall to the unit 1908, through the unit with magnetic interlock 1908 to the magnet 1912 and to the wireless charging unit 1910. The wireless charging unit 1910 can then wirelessly provide power to devices wirelessly on the transmissive tray above a coil in the wireless charger 1910. The power can also be used to power the UV driver that operates the UV source to provide UV light to the surfaces below the mobile device through the UV transmissive tray. In combination with the UV light provided by the UV source in unit 1908, a full 360 degrees of UV disinfection can be provided to devices positioned on the UV transmissive tray while the drawer is in a closed configuration. Further, when the drawer is in an open configuration, as depicted in FIG. 19, power is not routed to the wireless charger and lower UV source 1910. Further, power is not routed to the upper UV source, and instead is routed to a visible light source directed to the lighting zone 1914 depicted in FIG. 19. It is worth noting that the UV-C source in the unit 1908 can be oriented to project a lighting pattern internally such that when the drawer is closed, the UV light falls within the same general area UV zone 1914, with respect to the drawer. Alternatively, the magnetic interlock may merely communicate through magnet 1912 to wireless charger and UV source 1910 (or wirelessly communicate in a direct manner) to activate the UV source, with power for charging and UV source functionality provided by a battery instead of an electrical path from wall power.

Figure 20:
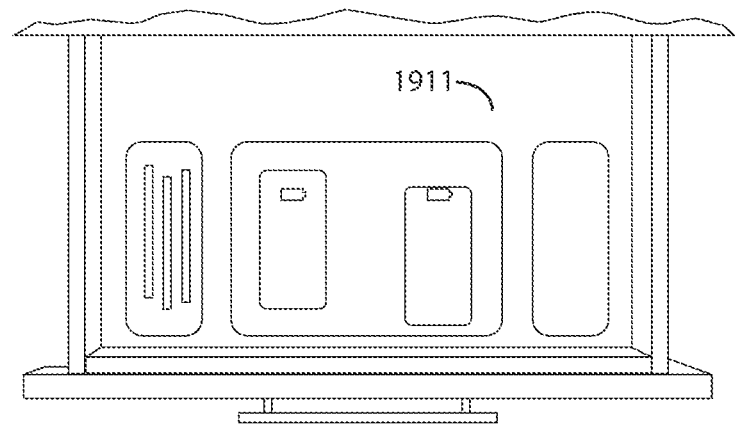
FIG. 20 illustrates a top view of the UV disinfection drawer with magnetic interlock of FIG. 19.

FIG. 20 illustrates a top view of an exemplary embodiment of the drawer of FIG. 19. The magnet 1912 and wiring to the wireless charger and UV source under tray 1911 is not visible from this view because it is either integrated into the face of the drawer or positioned behind the face of the drawer. The UV transmissive tray can include several pocket outlines for placing different wirelessly chargeable devices. Each UV transmissive tray pocket or outline can be aligned with a wireless power transmission coil configured to provide power at a distance through the tray to a device setting on the tray 1911. FIG. 20 shows a side perspective view where one of the drawer slides 1906 is shown positioned along the side of the drawer. Further, the combined general lighting, UV lighting, and magnetic interlock unit 108 is shown installed on the cabinet support between the width of the drawer.

Figure 21:
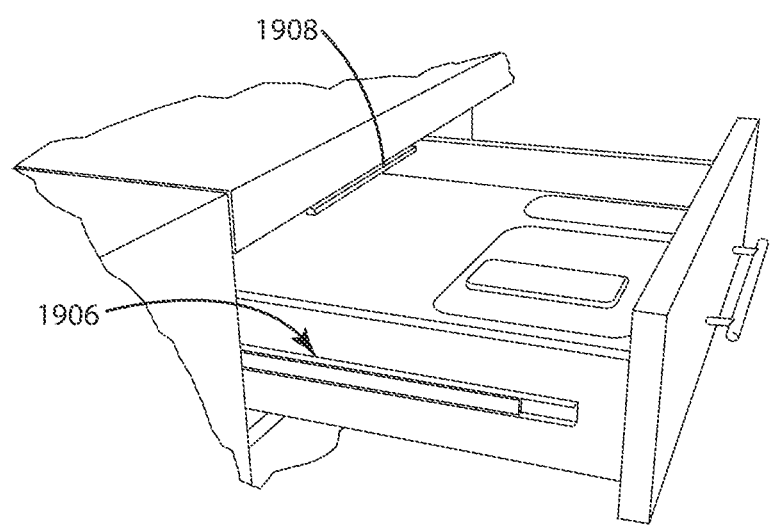
FIG. 21 illustrates a perspective side view of the UV disinfection drawer with magnetic interlock of FIG. 19.
Figure 22:
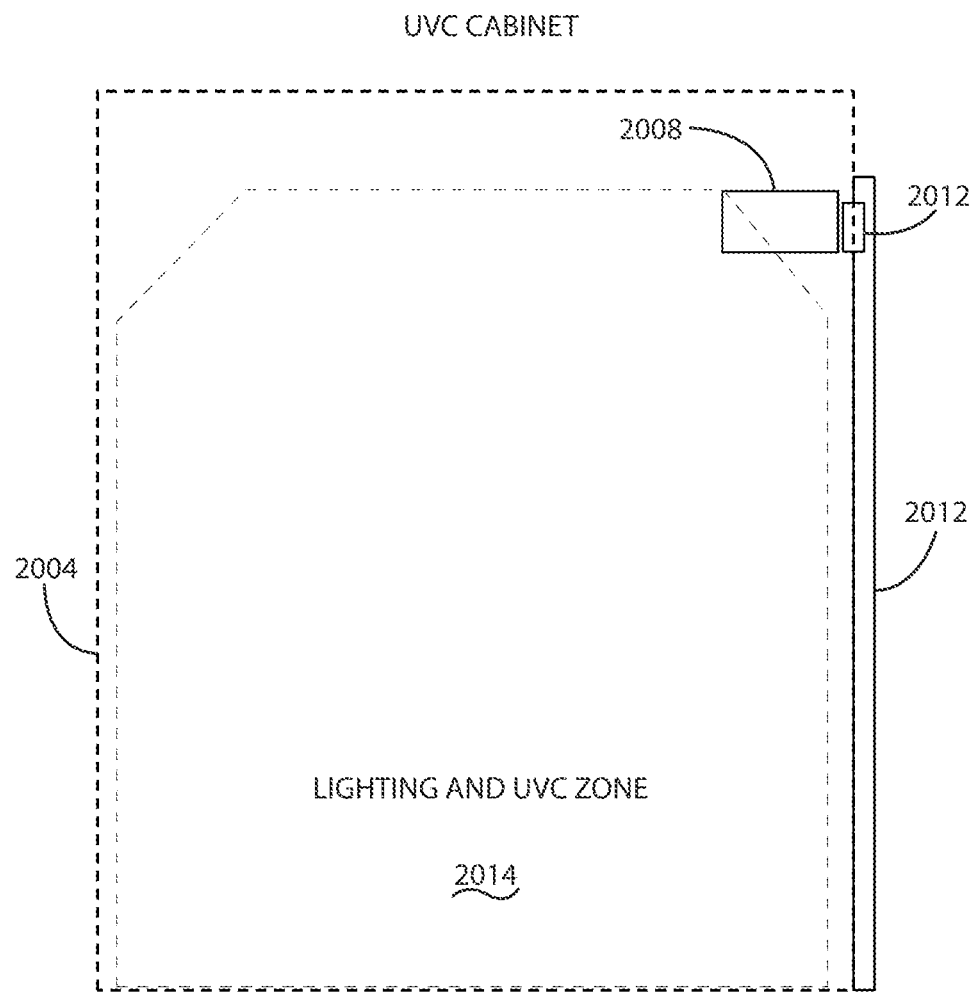
FIG. 22 illustrates a representative side sectional view of a UV disinfection cabinet with magnetic interlock in a closed configuration.
Figure 23:
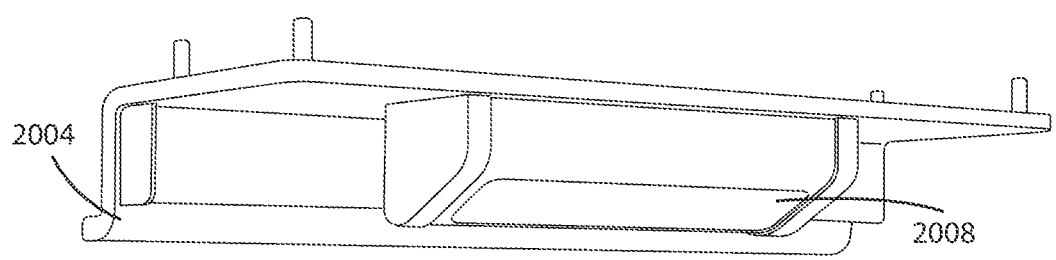
FIG. 23 illustrates a partial perspective view of a UV and visible light lighting unit mounted to a cabinet.

FIG. 22 illustrates a cabinet embodiment using a magnetic interlock. The cabinet 2004 is similar to the type where a garbage can may be stored. When the door 2012 is opened, the lighting unit 2008 can be activated to provide visible light on the cabinet contents (e.g. according to a control scheme such as timed, always on, or selectable). When the cabinet is closed the control circuit in the lighting unit 2008 can be configured to wait for about 10 seconds and then activate the UV source in the lighting unit 2008, for example to treat the area for about 6 minutes. The UV-C and lighting unit 2008 is similar to the one from the embodiment of FIGS. 19-21. The unit 20008 can be mounted to the cabinet 2004, e.g. the cabinet support, as perhaps best shown in the partial perspective view of FIG. 23. The depicted lighting unit 2008 is configured to cast visible light and UV light to the same general lighting and UVC zone 2014 within the cabinet. Further, magnet 2012 is mounted on the cabinet door such that when the door 2012 is closed the unit 2008 has a magnet that forms a magnetic interlock with the magnet 2012 and when the door 2012 is opened the magnet 2012 is moved away from the magnet in the unit 2008 such that the control circuit knows when the cabinet door is closed and open, and therefore when to activate the UV light or visible light.

Figure 24:
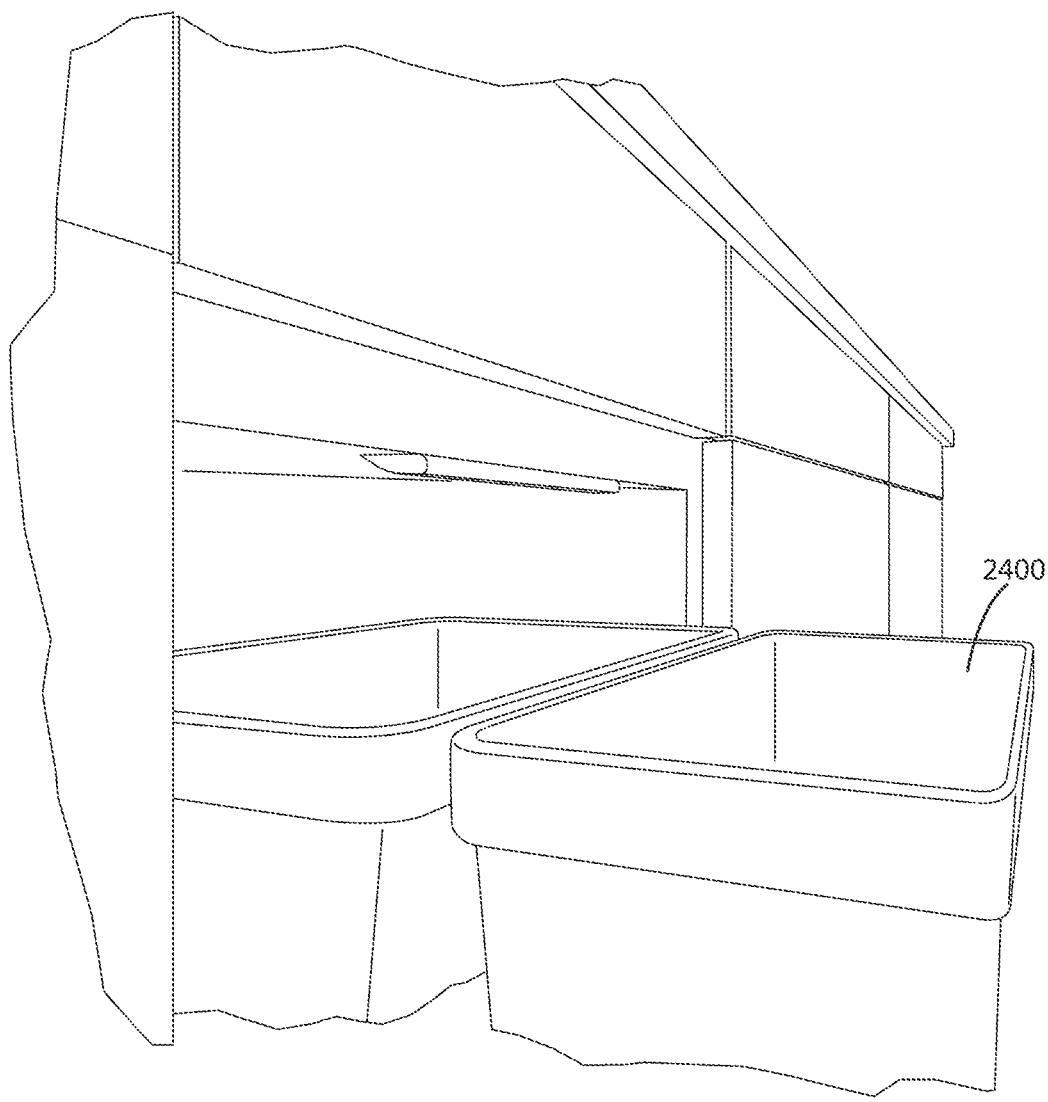
FIG. 24 illustrates a partial perspective view of a cabinet with a sliding garbage can extension with a UV and visible light lighting unit.
Figure 25:
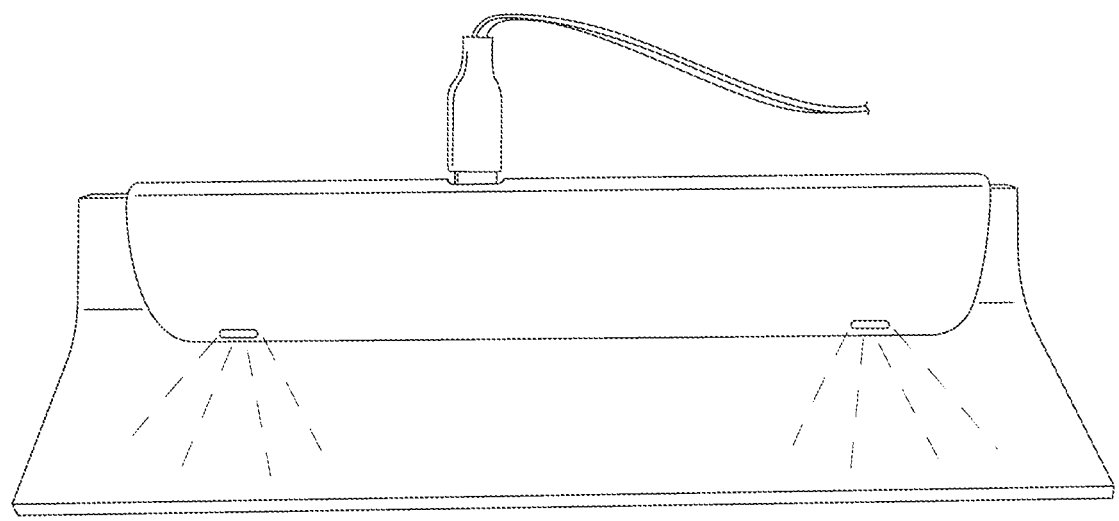
FIG. 25 illustrates a partial view of a UV and visible light lighting unit mounted to a portion of a cabinet support.

The cabinet can include a sliding extension that allows the face of the drawer to be pulled away from the face of the cabinet, for example to allow access to a garbage can 2400 or recycling can positioned on the sliding extension. When opened, the visible light can be activated, as depicted in FIG. 24. When closed, the UV light can be activated. FIG. 25 illustrates one embodiment of a lighting unit 2008 installed to a cabinet support or undercounter. In some embodiments it is designed to be reversible to enable frameless and framed mounting configurations.

The UV light, disinfection device, lens, or other components of some embodiments of the present disclosure can take the form or configuration of one of the UV lights, disinfection devices, lenses or other components described in U.S. Pat. No. 9,242,018 to Cole et al., which is entitled "PORTABLE LIGHT FASTENING ASSEMBLY" and issued on Jan. 26, 2016; U.S. Pat. No. 9,974,873 to Cole et al., which is entitled "UV GERMICIDAL SYSTEM, METHOD, AND DEVICE THEREOF" and issued on May 22, 2018; International application No. PCT/US2019/023842 to Baarman et al., which is entitled "DISINFECTION BEHAVIOR TRACKING AND RANKING" filed on Jun. 10, 2019; International application No. PCT/US2019/036298 to Baarman et al., which is entitled "MOBILE DEVICE DISINFECTION" was filed on Jun. 10, 2019, U.S. provisional patent application 62/924,324, filed on Oct. 22, 2019, to Baarman, entitled "OPTICAL PROPERTIES AND METHODS FOR UV TREATMENT", or U.S. provisional patent application 62/985,976, filed on Mar. 6, 2020, to Baarman et al., entitled "UV DISINFECTION PLATFORM", all of which are incorporated herein by reference in their entireties.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("AMC"), a field programmable gate array ("FPGA") or other programmable logic device, discrete gate or transistor logic, discrete hardware components, or any combination thereof designed to perform the functions described herein. Such components can be physically configured in any suitable manner, such as by mounting them to one or more circuit boards, or arranging them in other manners, whether combined into a single unit or distributed across multiple units. Similarly, steps of a method or process described herein may be embodied directly in hardware, in a software module executed by a processor, or in a combination thereof. A software module may reside in random access memory (RAM), flash memory, read-only memory (ROM), erasable programmable read-only memory (EPROM), electrically erasable programmable read-only memory (EEPROM), registers, hard disk, a removable disk, a CD-ROM, or any other form of storage medium known in the art. Although embodiments of the present invention have been described in detail, it will be understood by those skilled in the art that various modifications can be made therein without departing from the spirit and scope of the invention as set forth in the appended claims.

A controller, processor, computing, device, client computing device or computer, such as described herein, includes at least one or more processors or processing units and a system memory. The controller may also include at least some form of computer readable media. By way of example and not limitation, computer readable media may include computer storage media and communication media. Computer readable storage media may include volatile and nonvolatile, removable and non-removable media implemented in any method or technology that enables storage of information, such as computer readable instructions, data structures, program modules, or other data. Communication media may embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions and/or methods disclosed and claimed herein may be made and/or executed without undue experimentation in light of the present disclosure. While the compositions and methods of this invention have been described in terms of the embodiments included herein, it will be apparent to those of ordinary skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Thus, although particular embodiments have been described of the present invention, it is not intended that such references be construed as limitations upon the scope of this invention except as set forth in the following claims.

The embodiments of the invention in which an exclusive property or privilege is claimed are defined as follows:

1. A disinfection integrated circuit, the disinfection integrated circuit comprising:
    an LED driver module configured to drive a UV LED and a visible light LED;
    a sensor module configured to sense a user interaction at or proximal a surface of the integrated circuit;
    a communications module;
    a control circuit coupled to the sensor module, the LED driver module, and the communication module, wherein the control circuit is configured to:
        provide disinfection control signals to the LED driver module for automatic disinfection at or proximal the surface of the integrated circuit via a UV LED, wherein the disinfection control signals are based, at least in part, on output from the sensor module;
        provide feedback control signals to the LED driver module for providing visual feedback via a visible light LED, wherein the feedback control signals are based, at least in part, on output from at least one of the sensor module and the disinfection control signals; and
    wherein the sensor module is configured as a dynamic input control of a human machine interface, wherein the communication module is configured to transmit the dynamic input control to a human machine interface controller separate from the disinfection integrated circuit control circuit.

2. The disinfection and human machine interface integrated circuit of claim 1 wherein the control circuit is a state machine, the sensor module includes a capacitive touch sensor, wherein the LED driver module includes a UV LED driver configured to drive a UV LED, wherein the LED driver module includes a visible light LED driver configured to drive a plurality of RGB LEDs, and wherein the communications module is configured to communicate output related to output from the sensor module related to disinfection, human machine interface, or both to another device according to at least one of an I2C communication protocol, a CAN communication protocol, an RF communication protocol, a digital I/O communication protocol, a Smartthings communication protocol, a Zwave communication protocol, a communication protocol Zigbee, or any combination thereof.

3. The disinfection integrated circuit of claim 1 wherein the human machine interface is at least one of a push button, rotation, slide, or switch, or any combination thereof.

4. The disinfection integrated circuit of claim 1 wherein the sensor module includes a touch sensor configured to sense the user interaction at or proximal a surface of the integrated circuit, wherein the integrated circuit includes a plurality of visible light LEDs electrically coupled to the LED driver module to provide the visual feedback.

5. The disinfection integrated circuit of claim 4 wherein the visual feedback includes pathogen contamination status of the surface of the integrated circuit.

6. The disinfection integrated circuit of claim 5 wherein pathogen contamination status includes a dirty status, a clean status, and a disinfection in progress status.

7. The disinfection integrated circuit of claim 4 wherein the visual feedback includes error feedback and human machine interface feedback.

8. The disinfection integrated circuit of claim 4 wherein the visual feedback includes both pathogen contamination status and human machine interface feedback, wherein the disinfection integrated circuit control circuit is configured to provide the feedback control signals for providing pathogen contamination status and human machine interface feedback according to a lighting feedback control scheme.

9. The disinfection integrated circuit of claim 8 wherein the lighting visual feedback control scheme includes simultaneously indicating pathogen contamination status by adjusting at least one of intensity, color, and blinking of the visible light LEDs and indicating human machine interface feedback by adjusting a different one of at least intensity, color, and blinking of the visible light LEDs.

10. The disinfection integrated circuit of claim 8 wherein the lighting visual feedback control scheme includes simultaneously indicating pathogen contamination status by adjusting a characteristic of one of the visible light LEDs and indicating human machine interface feedback by adjusting a characteristic of a different one of the visible light LEDs.

11. The disinfection integrated circuit of claim 3 wherein the communication module is configured to receive feedback from a human machine interface controller separate from the disinfection integrated circuit control circuit, wherein the disinfection integrated circuit control circuit adapts the feedback control signals based, at least in part, on the received human machine interface controller feedback.

12. A disinfection and human machine interface integrated circuit, the disinfection and human machine interface integrated circuit comprising:
- an LED driver module configured to drive a UV LED and a visible light LED;
- a sensor module configured to sense a user interaction at or proximal a surface of the integrated circuit;
- a communications module;
- a control circuit coupled to the sensor module, the LED driver module, and the communication module, wherein the control circuit is configured to:
  - provide disinfection control signals to the LED driver module for automatic disinfection at or proximal the surface of the integrated circuit via a UV LED, wherein the disinfection control signals are based, at least in part, on output from the sensor module;
  - provide feedback control signals to the LED driver module for providing visual feedback via a visible light LED, wherein the feedback control signals are based, at least in part, on output from the sensor module; and
- wherein the sensor module is configured as an input control of a human machine interface and the communication module is configured to communicate the input control to a separate device, whereby the disinfection and human machine interface integrated circuit enables at least one of an automotive control input, a keyboard input, an elevator input, and a light switch input.

13. The disinfection and human machine interface integrated circuit of claim 12 wherein the LED driver module includes a separate UV LED driver and a separate visible light LED driver, wherein the control circuit is configured to provide control signals to the visible light LED driver for providing feedback to the user regarding the human machine interface.

14. A UV-C touch and feedback user interface module comprising:
- a protective covering having a UV and visible light transmissive portion that forms a touch surface of the module user interface;
- light emitting diodes (LEDs) including a UV LED and a visible light LED;
- a printed circuit board joined with the protective covering and the LEDs, the printed circuit board including:
  - a disinfection and human machine interface integrated circuit electrically coupled to the printed circuit board, the disinfection integrated circuit including:
    - an LED driver module configured to drive the LEDs;
    - a sensor module configured to sense a user interaction at or proximal the touch surface;
    - a communications module configured to communicate with an external device;
    - a control circuit coupled to the LED driver, the sensor module, and the communication module, wherein the control circuit is configured to:
      - provide disinfection control signals to the LED driver module for automatic disinfection at or proximal the touch surface via the UV LED transmitting UV-C light through the UV transmissive portion of the protective covering to the touch surface;
      - provide feedback control signals to the LED driver module for providing visual feedback via the visible light LED transmitting visible light through the protective covering to the touch surface; and
    - wherein the sensor module is configured as a dynamic input control of a human machine interface, wherein the communication module is configured to transmit the dynamic input to an external device separate from the disinfection and human machine interface integrated circuit, and wherein the communication module is configured to receive feedback from the external device, wherein the disinfection and human machine interface integrated circuit adapts the feedback control signals based, at least in part, on the received feedback from the external device.

15. The UV-C touch and feedback user interface module of claim 14 wherein the dynamic input control is at least one of a push button, rotation, slide, or switch, or any combination thereof.

16. The UV-C touch and feedback user interface module of claim 14 wherein the sensor module is configured as an input control of a human machine interface and the communication module is configured to communicate the input control to the separate device, whereby the disinfection and human machine interface integrated circuit enables at least one of an automotive control input, a keyboard input, an elevator input, a medical device input, and a light switch input.

17. A UV-C touch and feedback user interface module comprising:
- a protective covering having a UV and visible light transmissive portion that forms a touch surface of the module user interface;
- light emitting diodes (LEDs) including a UV LED and a visible light LED;
- a printed circuit board joined with the protective covering and the LEDs, the printed circuit board including:
  - a disinfection and human machine interface integrated circuit electrically coupled to the printed circuit board, the disinfection integrated circuit including:
    - an LED driver module configured to drive the LEDs;
    - a sensor module configured to sense a user interaction at or proximal the touch surface;
    - a communications module configured to communicate with a device separate from the disinfection and human machine interface integrated circuit;
    - a control circuit coupled to the LED driver, the sensor module, and the communication module, wherein the control circuit is configured to:
      - provide disinfection control signals to the LED driver module for automatic disinfection at or proximal the touch surface via the UV LED transmitting UV-C light through the UV transmissive portion of the protective covering to the touch surface;
      - provide feedback control signals to the LED driver module for providing visual feedback via the visible light LED transmitting visible light through the protective covering to the touch surface; and
- wherein the sensor module is configured as an input control of a human machine interface and the communication module is configured to communicate the input control to a device separate from the disinfection and human machine interface integrated circuit, whereby the disinfection and human machine interface integrated circuit enables a 3D moving interface.

* * * * *

UNITED STATES PATENT AND TRADEMARK OFFICE
CERTIFICATE OF CORRECTION

PATENT NO. : 11,911,530 B2
APPLICATION NO. : 17/909576
DATED : February 27, 2024
INVENTOR(S) : David W Baarman It is certified that error appears in the above-identified patent and that said Letters Patent is hereby corrected as shown below:

In the Claims

Column 29, Claim 11, Line 1:
"The disinfection integrated circuit of claim 3 wherein"
Should be:
– The disinfection integrated circuit of claim 1 wherein –

Signed and Sealed this
Second Day of April, 2024

Katherine Kelly Vidal
*Director of the United States Patent and Trademark Office*